United States Patent
Kocis et al.

(10) Patent No.: US 10,163,174 B2
(45) Date of Patent: *Dec. 25, 2018

(54) METHODS, SYSTEMS, AND COMPUTER PROGRAM PRODUCTS FOR EVALUATING A PATIENT IN A PEDIATRIC INTENSIVE CARE UNIT

(75) Inventors: Keith C. Kocis, Chapel Hill, NC (US); Daniel Joseph Kocis, Jr., Manorville, NY (US)

(73) Assignee: THE UNIVERSITY OF NORTH CAROLINA AT CHAPEL HILL, Chapel Hill, NC (US)

(*) Notice: Subject to any disclaimer, the term of this patent is extended or adjusted under 35 U.S.C. 154(b) by 1223 days.

This patent is subject to a terminal disclaimer.

(21) Appl. No.: 12/302,008

(22) PCT Filed: May 30, 2007

(86) PCT No.: PCT/US2007/012736
§ 371 (c)(1),
(2), (4) Date: Nov. 13, 2009

(87) PCT Pub. No.: WO2007/142968
PCT Pub. Date: Dec. 13, 2007

(65) Prior Publication Data
US 2010/0057490 A1    Mar. 4, 2010

Related U.S. Application Data

(60) Provisional application No. 60/809,283, filed on May 30, 2006.

(51) Int. Cl.
*G06Q 50/22* (2012.01)
*G06Q 50/24* (2012.01)
(Continued)

(52) U.S. Cl.
CPC ............ *G06Q 50/22* (2013.01); *G06F 19/00* (2013.01); *G16H 50/20* (2018.01); *G16H 50/30* (2018.01)

(58) Field of Classification Search
CPC ........ G06Q 50/22; G06Q 10/10; G06Q 50/24; G06Q 10/06; A61B 5/0205; A61B 5/7275;
(Continued)

(56) References Cited

U.S. PATENT DOCUMENTS 6,193,654 B1   2/2001   Richardson et al.
6,454,707 B1   9/2002   Casscells et al.
(Continued)

FOREIGN PATENT DOCUMENTS

WO   WO 2007/142968 A3   12/2007
WO   WO 2012/006174 A2    1/2012

OTHER PUBLICATIONS

Pollack et al., "Prism III: an updated Pediatric Risk of Mortality Score," Crit Care Medicine, vol. 24, No. 5, p. 743-752 (May 1996).
(Continued)

*Primary Examiner* — Maroun P Kanaan
(74) *Attorney, Agent, or Firm* — Jenkins, Wilson, Taylor & Hunt, P.A.

(57) ABSTRACT

Methods, systems, and computer program products for evaluating a patient in a pediatric intensive care unit (PICU) are disclosed. According to one aspect, a method may include collecting physiological data associated with a patient upon admission to a PICU and at least once after admission to the PICU. The physiological data may be associated with a statistical model, and a risk of mortality of the patient may be continually determined.

20 Claims, 29 Drawing Sheets

(51) Int. Cl.
    *G16H 50/30* (2018.01)
    *G16H 50/20* (2018.01)
    *G06F 19/00* (2018.01)
(58) Field of Classification Search
    CPC ... A61B 5/14551; A61B 5/024; A61B 5/0816;
        A61B 5/0022; A61B 5/1118; A61B 5/002;
        A61B 5/4094; A61B 5/412; G16H 50/30;
        G16H 50/20; G16H 50/50; G16H 10/60;
            G16H 40/20; G16H 80/00; G06F
            19/3431; G06F 19/3418; G06F 19/00;
            G06F 19/3437; G06F 19/3481; G06F
            19/3456; G06F 19/324; G06F 19/325
    USPC .......................................................... 705/2, 3
    See application file for complete search history.

(56) References Cited

U.S. PATENT DOCUMENTS

| | | |
|---|---|---|
| 2002/0193667 A1 | 12/2002 | McNair |
| 2005/0234313 A1 | 10/2005 | Rowlandson et al. |
| 2005/0234354 A1* | 10/2005 | Rowlandson et al. ......... 600/509 |
| 2006/0161459 A9* | 7/2006 | Rosenfeld et al. ............... 705/3 |
| 2006/0200009 A1 | 9/2006 | Wekell et al. |
| 2008/0214904 A1 | 9/2008 | Saeed et al. |
| 2013/0197924 A1 | 8/2013 | Kocis et al. |

OTHER PUBLICATIONS

Commonly Assigned, Co-Pending U.S. Appl. No. 13/721,010 titled "Methods, Systems, and Computer Readable Media for Evaluating a Hospital Patient's Risk of Mortality," (Unpublished, Filed Dec. 19, 2012).

Knaus et al., "The APACHE III prognostic system: Risk prediction of hospital mortality for critically ill hospitalized adults," Chest, 100, pp. 1619-1636 (1991).

Kruse et al., "Comparison of clinical assessment with APACHE II for predicting mortality risk in patients admitted to a medical intensive care unit," JAMA, 260(12), pp. 1739-1742 (1988).

Marcin et al., "Combining physician's subjective and physiology-based objective mortality risk predictions," Crit Care Med, 28(8), pp. 3113-3114 (2000).

Rocker et al., "Clinician predictions of intensive care unit mortality," Crit Care Med, 32(5), pp. 1149-1154 (2004).

Smith et al., "Hospital wide physiological surveillance—a new approach to the early identification and management of the sick patient," Resuscitation, 71(1), pp. 19-28 (Oct. 2006).

Tarassenko et al., "Integrated monitoring and analysis for early warning of patient deterioration," Br J Anaesth, 97, pp. 64-68 (2006).

Watkinson et al., "A randomized controlled trial of the effect of continuous electronic physiological monitoring on the adverse event rate in high risk medical and surgical patients," Anaesthesia 61, pp. 1031-1039 (2006).

Yien et al., "Spectral analysis of systemic arterial pressure and heart rate signals as a prognostic tool for the prediction of patient outcome in the intensive care unit," Crit Care Med, 25, pp. 258-266 (1997).

Notification of Transmittal of the International Search Report and the Written Opinion of the International Searching Authority, or the Declaration for International Patent Application No. PCT/US2011/042416 (Feb. 24, 2012).

Notification of Transmittal of the International Search Report and the Written Opinion of the International Searching Authority, or the Declaration for International Application No. PCT/US2007/012736 (Dec. 31, 2007).

Artemis™ Healthcare, "Real-Time, Cognitive Analytics," pp. 1-2 (publication date unknown).

Brilli et al., "Implementation of a medical emergency team in a large pediatric teaching hospital prevents respiratory and cardiopulmonary arrests outside the intensive care unit," Pediatr Crit Care Med 8(3), pp. 236,46; quiz 247 (May 2007).

Buist et al., "Effects of a medical emergency team on reduction of incidence of and mortality from unexpected cardiac arrests in hospital: preliminary study," BMJ 324(7334), pp. 387-390 (Feb. 16, 2002).

Duncan et al., "The Pediatric Early Warning System score: a severity of illness score to predict urgent medical need in hospitalized children," J Crit Care, 21(3), pp. 271-278 (Sep. 2006).

Goldberger, "Non-linear dynamics for clinicians: Chaos theory, fractals, and complexity at the bedside," Lancet, 347, pp. 1312-1314 (1996).

Goldstein et al., "Physiologic Data Acquisition System and Database for the Study of Disease Dynamics in the Intensive Care Unit," Crit Care Medicine, vol. 31, No. 2, p. 433-441 (2003).

Gordon et al., "Heart-rate spectral analysis: A noninvasive probe of cardiovascular regulation in critically ill children with heart disease," Pediatric Cardio, 9, pp. 69-77 (1988).

Griffin et al., "Heart Rate Characteristics: Novel Physiomarkers to Predict Neonatal Infection and Death," Pediatrics, 116(5), pp. 1070-1074 (Nov. 2005).

Honzikova et al., "Baroreflex sensitivity determined by spectral method and heart rate variability and two-years mortality in patients after myocardial infarction," Physiol Res, 49, pp. 643-650 (2000).

Hravnak et al., Defining the Incidence of Cardiorespiratory Instability in Patients in Step-down Units Using an Electronic Integrated Monitoring System Arch Intern Med, 168(12), pp. 1300-1308 (Jun. 23, 2008).

Kleiger et al., "Heart rate variability: measurement and clinical utility," ANE, 10(1), pp. 88-101 (2005).

Pomeranz et al., "Assessment of autonomic function in humans by heart rate spectral analysis," Am J Physiol, 248:H, pp. 151-153 (1985).

Randolph et al., "Growth of pediatric intensive care units in the United States from 1995 to 2001," J Pediatr, 144(6), pp. 792-798 (2004).

Shann et al., "Paediatric index of mortality (PIM): a mortality prediction model for children in intensive care," Intensive Care Med, 23(2), pp. 201-207 (Feb. 1997).

Slater et al., "PIM2: a revised version of the Paediatric Index of Mortality," Intensive Care Med, 29(2), pp. 278-285 (Feb. 2003).

Wessel et al., "Evaluation of renormalized entropy for risk stratification using heart rate variability data," Med Biol Eng Comput, 38, pp. 680-685 (2000).

* cited by examiner

| QTMS V3.2 | INTERVALS AND THEIR CODED VARIABLES OF PROJECT CHART THAT HAVE RESPONSE RATES SIGNIFICANTLY HIGHER OR LOWER (WITH 95% CONFIDENCE) THAT THE OVERALL RESPONSE RATE +/- 20% | | | | | | |
|---|---|---|---|---|---|---|---|
| —VARIABLE— CODED | ORIGINAL | INTERVAL | NO. OF SOLICITED | NO. OF RESPS. | —RESPONSE— RATE | INDEX | INDEX OF THE 95% CONFIDENCE INTERVAL'S CLOSEST POINT TO THE OVERAL RESPONSE RATE |
| D1 | PUPILS | 1-2 | 315 | 315 | 100.00 | 182 | 182 ************************** |
| D2 | TEMP | 30.9-35.1 | 138 | 137 | 99.28 | 181 | 178 ************************ |
| D3 | EPI | 1 | 551 | 544 | 98.73 | 180 | 176 *********************** |
| D4 | GCS | 3 | 470 | 442 | 94.04 | 171 | 167 ********************* |
| D5 | TEMP | 35.2-36 | 167 | 155 | 92.81 | 169 | 162 ******************* |
| D6 | GLUCOSE | 143-146 | 37 | 35 | 94.59 | 172 | 159 ****************** |
| D7 | GLUCOSE | 139-142 | 33 | 31 | 93.94 | 171 | 156 ****************** |
| D8 | GLUCOSE | 134-138 | 34 | 31 | 91.18 | 166 | 149 **************** |
| D9 | DOPAMINE | 1 | 570 | 475 | 83.33 | 152 | 146 *************** |
| D10 | PIO2 | 0.45-0.58 | 193 | 162 | 83.94 | 153 | 144 ************** |
| D11 | GLUCOSE | 148-155 | 33 | 28 | 84.85 | 155 | 132 ********** |
| D12 | OTHER | 1 | 392 | 298 | 76.02 | 139 | 131 ********** |
| D13 | GCS | 12-15 | 333 | 126 | 37.84 | 69 | 78 ******* |
| D14 | GCS | 4-7 | 237 | 84 | 35.44 | 65 | 76 ****** |
| D15 | GCS | 10-11 | 420 | 150 | 35.05 | 64 | 72 ***** |
| D16 | GLUCOSE | 217-367 | 19 | 4 | 21.05 | 38 | 72 ***** |
| D17 | SYSTOLIC | 82-98 | 56 | 15 | 26.79 | 49 | 70 ***** |
| D18 | EPI | 0 | 1189 | 416 | 34.99 | 64 | 69 **** |
| D19 | SYSTOLIC | 74-80 | 59 | 15 | 25.42 | 46 | 67 **** |
| D20 | TEMP | 37.4-36 | 152 | 44 | 28.95 | 53 | 66 **** |
| D21 | PIO2 | 0.22-0.26 | 223 | 66 | 29.60 | 54 | 65 *** |
| D22 | TEMP | 38.1-39.6 | 68 | 14 | 20.59 | 38 | 55 * |

FIG. 7

| QTMS V3.2 | INTERPRETATION OF THE FACTOR STRUCTURE COMPLETENESS OF THE FACTOR SOLUTION: 82.54 | | | | | |
|---|---|---|---|---|---|---|
| FACTOR # | % VARIANCE EXPLAINED | VARIABLE | HIGHEST LOAD | COMMUNALITY  100%--▶ | SECOND LOAD | HIGHEST & FACTOR |
| 1 | 17.7 | D2 (TEMP: 30.9-35.1) | 0.77881 | 83.2 ***************** | -0.39056 | 2 |
|  |  | D4 (GCS,3) | 0.77471 | 81.4 ***************** | 0.36515 | 2 |
|  |  | D3 (EPI,1) | 0.76815 | 88.1 ***************** | 0.34739 | 4 |
|  |  | D9 (DOPAMINE:1) | 0.70872 | 72.9 **************** | 0.22993 | 4 |
|  |  | D18 (EPI,0) | -0.70414 | 83.9 ***************** | -0.38040 | 4 |
|  |  | D1 (PUPILS:1-2) | 0.65118 | 78.7 **************** | 0.51098 | 2 |
|  |  | D10 (FIO2: 0.45-0.58) | 0.60700 | 60.3 ************ | 0.36033 | 10 |
| 2 | 6.7 | D5 (TEMP: 35.2-36) | 0.87249 | 81.5 **************** | 0.19786 | 1 |
| 3 | 6.0 | D13 (GCS: 12-15) | 0.78088 | 81.4 ***************** | -0.32036 | 1 |
|  |  | D15 (GCS: 10-11) | -0.73772 | 86.6 ****************** | -0.34306 | 1 |
| 4 | 5.8 | D6 (GLUCOSE: 143-146) | 0.84874 | 77.9 **************** | 0.12862 | 5 |
| 5 | 5.6 | D14 (GCS: 4-7) | 0.93248 | 90.9 ****************** | 0.12046 | 4 |
| 6 | 5.3 | D17 (SYSTOLIC 82-98) | 0.88893 | 82.5 **************** | -0.12746 | 6 |
|  |  | D21 (FIO2: 0.22-0.28) | 0.53395 | 64.3 ************ | 0.46545 | 6 |
| 7 | 5.3 | D7 (GLUCOSE: 139-142) | 0.91441 | 86.6 ****************** | -0.09886 | 4 |
| 8 | 5.2 | D19 (SYSTOLIC: 74-90) | 0.91189 | 86.1 ***************** | -0.08747 | 6 |
| 9 | 5.1 | D20 (TEMP: 37.4-30) | 0.92235 | 88.8 ***************** | -0.11226 | 12 |
|  |  | D12 (OTHER: 1) | -0.44887 | 77.5 **************** | -0.36680 | 12 |
| 10 | 5.1 | D11 (GLUCOSE: 148-155) | 0.93431 | 88.0 ***************** | 0.06530 | 1 |
| 11 | 5.0 | D8 (GLUCOSE: 134-138) | 0.96953 | 94.6 ******************* | -0.04281 | 4 |
| 12 | 4.9 | D22 (TEMP: 38.1-39.6) | 0.90260 | 87.5 ***************** | 0.13483 | 13 |
| 13 | 4.7 | D22 (GLUCOSE: 217-367) | 0.94567 | 92.9 ******************* | 0.11763 | 12 |

FIG. 8

SINGLE FACTOR SCAN  
TYPE IS "CONTINUOUS"

RESULT

QTMC  
V3.2

| # | INTERVAL | NO. OF SOLICITED | NO. OF RESPONDERS | RESPONSE RATE | CHISQ | PROB. | RESPONSE INDEX | |
|---|---|---|---|---|---|---|---|---|
| 1 | 25-37 | 43 | 40 | 93.023 | 4.226 | 0.0398 | 138 | ***************** |
| 2 | 98-47 | 44 | 28 | 86.364 | 2.2754 | 0.1222 | 128 | *************** |
| 3 | 94-49 | 42 | 29 | 92.857 | 4.075 | 0.0405 | 130 | **************** |
| 4 | 51-70 | 43 | 30 | 69.767 | 0.038 | 0.8438 | 104 | ************ |
| 5 | 71-94 | 47 | 11 | 23.361 | 11.121 | 0.0009 | 30 | * |
| 6 | 95-110 | 44 | 26 | 59.091 | 0.441 | 0.5067 | 80 | ********* |
| 7 | 111-127 | 44 | 20 | 45.455 | 1.221 | 0.0772 | 68 | ***** |
| 8 | 128-146 | 42 | 36 | 61.905 | 0.182 | 0.6698 | 92 | ********** |
| 9 | 147-168 | 43 | 21 | 72.092 | 0.147 | 0.7038 | 107 | ************ |
| 10 | 166-148 | 21 | 21 | 67.742 | 0.001 | 0.9762 | 102 | *********** |
|   |   | 419 | 282 | 57.303 | 25.738 | 0.0023 | 100 | |

| | TOTAL N | N | N MISSING | MEAN | STD. DEV. | MINIMUM | MAXIMUM | C.V. |
|---|---|---|---|---|---|---|---|---|
| ALL OBSERVATIONS | 419 | 419 | 0 | 97.7341766 | 62.3442688 | 25 | 493 | 63.78 |
| NON-RESPONDERS | 137 | 137 | 0 | 110.387664 | 57.0186679 | 20 | 493 | 51.67 |
| RESPONDERS | 282 | 282 | 0 | 91.6212059 | 63.9788562 | 25 | 462 | 69.82 |

| | F | PROG=F | VARIANCES | T | DF | PROB>[T] |
|---|---|---|---|---|---|---|
| T TEST FOR COMPARING THE MEANS OF | | | UNEQUAL | 3.0381 | 299.1 | 0.0037 |
| THE RESPONDERS AND NON-RESPONDERS | 1.2590 | 0.1290 | EQUAL | 2.9082 | 417.0 | 0.0036 |

| # | INTERVAL | NO. OF SOLICITED | NO. OF RESPONDERS | CONFIDENCE INTERVAL AT 95% | | | |
|---|---|---|---|---|---|---|---|
| | | | | LEFT END | R.RATE | RIGHT END | |
| 1 | 25-37 | 43 | 40 | 85.405 | 93.023 | 100.00 | ⊢*⊣ |
| 2 | 30-43 | 44 | 28 | 76.224 | 86.364 | 96.504 | ⊢*⊣ |
| 3 | 44-49 | 42 | 29 | 85.068 | 92.857 | 100.00 | ⊢*⊣ |
| 4 | 51-70 | 43 | 30 | 36.040 | 69.767 | 83.495 | ⊢--*--⊣ |
| 5 | 71-94 | 47 | 11 | 12.340 | 23.361 | 36.623 | ⊢--*--⊣ |
| 6 | 95-110 | 44 | 26 | 44.563 | 59.091 | 73.618 | ⊢---*---⊣ |
| 7 | 111-127 | 44 | 20 | 30.742 | 45.455 | 60.167 | ⊢---*---⊣ |
| 8 | 128-146 | 42 | 36 | 47.218 | 61.905 | 75.591 | ⊢---*---⊣ |
| 9 | 147-168 | 43 | 21 | 38.686 | 72.092 | 85.500 | ⊢---*---⊣ |
| 10 | 166-148 | 21 | 21 | 31.216 | 67.742 | 94.198 | ⊢---*---⊣ |
|   |   | 419 | 282 | 62.811 | 71.705 | | Q.R.R |

*FIG. 13*

| DATE | TIME | FiO2 | GCS | Pupils | glucose | Urine output | temperature | Dopamine | Epi | other |
|---|---|---|---|---|---|---|---|---|---|---|
| 12/16/2005 | 20:00 | 0.6 | 3 | 2 | 138 | 464 | 38.9 | 0 | 1 | 0 |
| 12/16/2005 | 21:00 | 0.4 | 3 | 2 | 143 | 25 |  | 0 | 1 | 0 |
| 12/16/2005 | 22:00 | 0.3 | 3 | 2 | 136 | 30 | 39.1 | 0 | 1 | 0 |
| 12/16/2005 | 23:00 | 0.3 | 3 | 2 |  | 7 | 38.7 | 0 | 1 | 0 |
| 12/16/2005 | 0:00 | 0.3 | 3 | 2 |  | 10 | 38.1 | 0 | 1 | 0 |
| 12/17/2005 | 1:00 | 0.3 | 3 | 2 | 137 | 20 | 37.8 | 0 | 1 | 0 |
| 12/17/2005 | 2:00 | 0.3 | 3 | 2 |  | 30 | 37.2 | 0 | 1 | 0 |
| 12/17/2005 | 3:00 | 0.25 | 3 | 2 |  | 60 | 37 | 0 | 1 | 0 |
| 12/17/2005 | 4:00 | 0.25 | 3 | 2 | 139 | 60 | 36.5 | 0 | 1 | 0 |
| 12/17/2005 | 5:00 | 0.25 | 3 | 2 |  |  | 35.8 | 0 | 1 | 0 |
| 12/17/2005 | 6:00 | 0.25 | 3 | 2 |  | 125 | 35.6 | 0 | 1 | 0 |
| 12/17/2005 | 7:00 | 0.25 | 3 | 2 |  |  | 35.6 | 0 | 1 | 0 |
| 12/17/2005 | 8:00 | 0.25 | 3 | 2 | 137 | 105 | 36.2 | 0 | 1 | 0 |
| 12/17/2005 | 9:00 | 0.25 | 3 | 2 |  | 21 | 36.7 | 0 | 1 | 0 |
| 12/17/2005 | 10:00 | 0.25 | 3 | 2 |  | 100 | 37.3 | 0 | 1 | 0 |
| 12/17/2005 | 11:00 | 0.25 | 3 | 2 |  | 45 | 37.3 | 0 | 0 | 0 |
| 12/17/2005 | 12:00 | 0.25 | 3 | 2 |  | 40 | 37.2 | 0 | 0 | 0 |
| 12/17/2005 | 13:00 | 0.25 | 3 | 2 | 137 |  | 37.1 | 0 | 0 | 0 |
| 12/17/2005 | 14:00 | 0.25 | 3 | 2 | 141 | 125 |  | 0 | 0 | 0 |

FIG. 14

SINGLE FACTOR SCAN  
TYPE IS "CONTINUOUS"  
EPI  
QTMC V3.2

| # | INTERVAL | NO. OF SOLICITED | NO. OF RESPONDERS | RESPONSE RATE | CHISQ | PROB. | RESPONSE INDEX | |
|---|---|---|---|---|---|---|---|---|
| 1 | . | 97 | 48 | 49.485 | 0.513 | 0.4738 | 90 | **** |
| 2 | 0 | 1189 | 416 | 34.287 | 85.678 | 0.0000 | 64 | * |
| →3 | 1 | 551 | 554 | 98.730 | 193.147 | 0.0000 | 180 | ****************** |
| | | 1837 | 1008 | 54.872 | 279.338 | 0.0000 | 100 | |

SINGLE FACTOR SCAN  
TYPE IS "CONTINUOUS"  
GCS  
QTMC V3.2

| # | INTERVAL | NO. OF SOLICITED | NO. OF RESPONDERS | RESPONSE RATE | CHISQ | PROB. | RESPONSE INDEX | |
|---|---|---|---|---|---|---|---|---|
| 1 | . | 146 | 80 | 54.795 | 0.000 | 0.9899 | 100 | ***** |
| →2 | 3 | 470 | 442 | 94.043 | 131.421 | 0.0000 | 171 | ****************** |
| 3 | 4-7 | 237 | 84 | 35.443 | 16.304 | 0.0001 | 65 | * |
| 4 | 8-9 | 223 | 126 | 56.502 | 0.106 | 0.7424 | 103 | ****** |
| 5 | 10-11 | 428 | 150 | 35.047 | 30.657 | 0.0000 | 64 | * |
| 6 | 12-15 | 333 | 126 | 37.838 | 17.609 | 0.0000 | 69 | * |
| | | 1837 | 1008 | 54.872 | 196.100 | 0.0000 | 100 | |

SINGLE FACTOR SCAN  
TYPE IS "CONTINUOUS"  
PUPILS  
QTMC V3.2

| # | INTERVAL | NO. OF SOLICITED | NO. OF RESPONDERS | RESPONSE RATE | CHISQ | PROB. | RESPONSE INDEX | |
|---|---|---|---|---|---|---|---|---|
| 1 | . | 116 | 53 | 45.690 | 1.782 | 0.1818 | 83 | * |
| 2 | 0 | 1406 | 640 | 45.519 | 22.414 | 0.0000 | 83 | * |
| →3 | 1-2 | 315 | 315 | 100.00 | 116.910 | 0.0000 | 182 | ****************** |
| | | 1837 | 1008 | 54.872 | 141.106 | 0.0000 | 100 | |

*FIG. 15*

METHODS, SYSTEMS, AND COMPUTER PROGRAM PRODUCTS FOR EVALUATING A PATIENT IN A PEDIATRIC INTENSIVE CARE UNIT

RELATED APPLICATIONS

This application claims the benefit of U.S. Provisional Patent Application Ser. No. 60/809,283, filed May 30, 2006, the disclosure of which is incorporated herein by reference in its entirety.

GOVERNMENT INTEREST

This invention was made with government support under Grant Number HD049935 awarded by the National Institutes of Health. The government has certain rights in the invention.

TECHNICAL FIELD

The subject matter disclosed herein relates generally to patient evaluation. More particularly, the subject matter disclosed herein relates to evaluating a patient in a pediatric intensive care unit (PICU).

BACKGROUND

Intensive care units (ICUs) commonly include patient monitoring systems for monitoring patient status and condition. Typical patient monitoring systems include a monitor having one or more detectors attached to a patient for detecting parameters, such as electrocardiogram (ECG) signals, blood pressure, blood oxygen, blood glucose, and temperature. The output from the detectors is sent to a system processor, which subsequently processes the measured values. These values may then be displayed on a display screen or stored for later analysis. Data representing the measured physiological parameters can be displayed as waveforms and/or numerical values. ICUs provide advanced monitoring capabilities for enabling medical practitioners to evaluate the clinical status of patients and track their response to a wide range of interventions.

One of the important functions of an ICU is to provide advanced monitoring capabilities to evaluate the clinical status of patients and to track their responses to a wide range of interventions. Morbidity and mortality have diminished dramatically in PICUs across the United States due to advancements in medical and surgical therapeutics, life saving pharmaceuticals, and training of medical practitioners. Standard monitoring systems present physiological data such as intermittent or continuous core temperature, invasive arterial blood pressure, continuous invasive central venous pressure, continuous pulsed oximetry, and continuous end tidal carbon dioxide concentrations. However, current monitoring systems do not present these data in a format that fosters understanding of the complex dynamic changes occurring instantaneously or over time in a biological system. Simple, time domain measures of heart rate and respiratory rate are typically displayed as: 3-5 second mean values; mean values of parameters plotted against time; or alarms for out of range values determined by manufacturers or modified by medical practitioners. These values are often not scaled to reflect age or diagnosis adjusted norms for children. For these reasons, the need for advancement of monitoring devices is great.

A variety of advanced organ specific monitoring devices have emerged over recent years with mixed utility and acceptance in the PICU. Measurements made with these devices include: continuous cardiac output measurements; thoracic electrical bioimpedance continuous cardiac output; continuous in vivo arterial blood gas analysis; continuous pulmonary mechanics and ventilator parameters; continuous venous oxygen saturation measurement; and continuous processed electroencephalographic analysis. These measurements have provided additional information to the bedside clinician, but most have failed to demonstrate improvement in patient morbidity or mortality. Each of these monitoring devices provides a unidimensional time domain appraisal of a specific organ function that must be assimilated, interpreted, and acted upon by the bedside physician, nurse, or allied health care worker. It is desirable to provide improvements for presenting this information and analysis of this information to medical practitioners.

As mentioned above, some PICU monitoring equipment generates alarms when patient physiological data falls outside of an excepted range. However, because these alarms are often based on individual parameters and not based on accurately weighted groups of parameters, false positives often occur. Because of the high frequency of false positives, alarms generated based on individual physiological measurements are often ignored by PICU staff.

Software tools are available for evaluating a patients risk of mortality. However, conventional tools only evaluate a patient's risk of mortality based on parameters collected upon admission to the PICU. There is no updating of the risk of mortality based on physiological measurements after the patient has been admitted to PICU. As a result, conventional tools do not provide any post care evaluation of a patient's risk of mortality.

Accordingly, there exists a long felt need for methods, systems, and computer program products for evaluating a patient in a PICU.

SUMMARY

According to one aspect, the subject matter described herein comprises systems, methods, and computer program products for evaluating a patient in a PICU. One method may include collecting physiological data associated with a patient upon admission to a PICU and at least once after admission to the PICU. The physiological data may be analyzed with a statistical model. Further, a risk of mortality of the patient can be continually determined.

According to another aspect, the subject matter described herein comprises systems, methods, and computer program products for selecting a physiological variable for use in evaluating risk of mortality of a patient in a PICU. One method may include receiving survival outcome data and multivariate physiological data associated with a patient in a PICU. The survival outcome data and the multivariate physiological data may be analyzed with a statistical model to identify a physiological variable affecting risk of mortality of the patient.

BRIEF DESCRIPTION OF THE DRAWINGS

Exemplary embodiments of the subject matter will now be explained with reference to the accompanying drawings, of which:

FIG. 7 is a chart of 22 intervals obtained from 11 raw variables in accordance with an embodiment of the subject matter disclosed herein;

FIG. 8 are results of an orthoganized list of the data shown in the chart of FIG. 7;

FIG. 13 is a chart profiling extreme derogatory ranges within a battery of laboratory tests;

FIG. 14 is a chart of an example of intermittent physiologic parameters and clinical signs;

FIG. 15 includes charts profiling examples of intermittent physiologic parameters and clinical signs evaluated through QTMS with selected best results;

DETAILED DESCRIPTION

Figure 1:
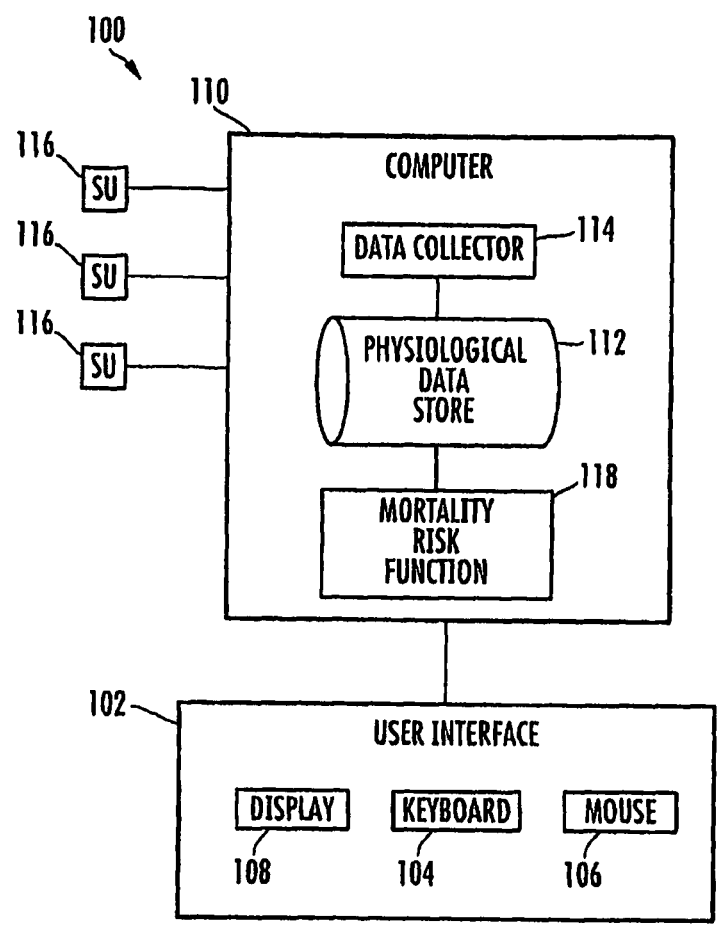
FIG. 1 is an exemplary block diagram of a patient monitoring system for evaluating a patient in a PICU according to an embodiment of the subject matter described herein.

The subject matter disclosed herein is directed to systems, methods, and computer program products for evaluating a patient in a PICU. Particularly, a patient evaluation may include continually determining a risk of mortality of a PICU patient based on physiological data associated with the patient. The physiological data may be collected upon admission to the PICU and at least once after admission to the PICU. Further, the physiological data may be analyzed with a statistical model, and the risk of mortality of the patient may be continually determined. The risk of mortality may be continuously updated and presented to a medical practitioner via a user interface. By presenting up-to-date information regarding the risk of mortality and the physiological data contributing to that risk, patient outcomes are expected to improve.

According to one aspect, systems, methods, and computer program products disclosed herein may be utilized for selecting a physiological variable for use in evaluating mortality risk of a patient in a PICU. A method may include receiving survival outcome data and multivariate physiological data associated with a patient in a PICU. The survival outcome data and the multivariate physiological data can be analyzed with a statistical model to identify a physiological variable affecting mortality risk of the patient. A weight may be assigned to the physiological variable for use with the statistical model in determining a risk of mortality of the patient.

The risk of mortality may be determined by collecting physiological data from various sources, by integrating or combining the data from the various sources, and by analyzing the data as disclosed herein. Physiological signals encode information which characterizes the spectrum from normal to disease conditions in living systems. Physicians are trained to recognize diagnostic patterns in these signals. Signal processing methodologies enhance diagnostic capabilities through either detection of information not otherwise perceptible, or quantification of physiological measures leading to diagnostic differentiation of sickness from health. Such signal processing methodologies may be used to detect or identify physiological data for use in determining a risk of mortality. Signal processing techniques may be broadly categorized as spectral and time series methodologies, while wavelets span the two approaches. Time series methods may be linear or non-linear, stationary or non-stationary, and/or parametric or non-parametric. Signal processing methods presume stationarity, while non-linear methods, such as bispectral analysis, may be applied to diagnostics.

Neural networks may be trained to recognize patterns derived from physiological signals using characteristics derived from any signal processing methodology, which are linked to health and disease states, or trends toward either. Applications of bispectral methods may be used to detect nonlinear trends in critically ill patients. Heart rate variability using linear signal processing techniques may be used for real time analysis of spectral bands which characterize autonomic activity. This approach provides a quantitative measure of autonomic activity as a trend as patients progress toward health or disease. Detection of trends may be enhanced using cross spectral quantification of interactions between physiological signals determined continuously in real time. This technique may be applied for determining signal artifact (noise) from significant changes in clinical state (signal).

Data mining is another technique useful to collect physiological data for use in determining a risk of mortality. Data mining is an extension of statistical hypothesis testing. Neural networks and data intensive mining may be used together for sorting and analyzing physiological data for evaluation of a patient as disclosed herein. A goal of data mining is to construct a mathematical algorithm that captures viable representations of existing phenomena hidden with a database. Different classes of algorithms may include standard regression, rule induction, and neural networks. In addition, a model comparison module can provide a cross comparison among multiple models based upon receiver operator curve (ROC) characteristics.

Physiological data may be collected from patient charts, laboratory tests, and monitoring equipment. Real time continuous physiological signals, such as electrocardiogram (ECG) signals (e.g., invasive arterial blood pressure and invasive central venous pressure), may be collected and analyzed. Further, an analysis can be performed to determine advanced measures of the variability of continuous physiological signals. For example, a spectral analysis (also referred to as power spectral analysis or auto spectral analysis) may be performed on the ECG signals. Other physiological data that may be collected includes measures of organ function, such as serum glucose and the like, and their variability.

Spectral analysis of heart rate variability may be used in determining a risk of mortality. In both adults and children, spectral analysis of heart rate variability may be used to quantify the dynamic, physiologic changes occurring in a wide variety of critical illnesses, such as shock, severe head trauma, post operative congenital heart disease, acute myocardial, infarction, and diabetes. The concept is that healthy biological systems are in a natural state of "chaos" and when critical illness develops, this natural variability is lost. Analysis of the low frequency and high frequency spectral content of heart rate variability with calculation of a ratio of these two areas may be used as a predictor of mortality in children. Particularly, these measurements can be indicators of sympathetic and parasympathetic neuromodulation of the heart. Coupling these measurements into a multivariate predictor of mortality as disclosed herein may improve the predictive capability of continuous physiologic monitoring. As a result, this predictive information may improve the outcome of critically ill patients in ICU.

Another predictor of risk of mortality includes power spectral analyses of arterial blood pressure. Blood pressure modulates both stroke volume and heart rate through the baroreflexes, which are modulated by respiration, reflecting the integrity of the brain stem control of cardio-reflexes. Variability analysis of continuously measured invasive arterial blood pressure may be used for determining patient outcome such as, for example, in relation to heart rate and respiratory variability. Trends of increasing power in low frequency and very low frequency bands in both heart rate and blood measurements may be used for predicting mortality or instability in critically ill patients.

Other exemplary physiological data that may be used in determining risk of mortality includes demographic data and diagnosis related predictors of mortality. Examples of demographic and diagnosis related predictors of mortality include patient age and sex, any of various general diagnostic groups, and pre-IDC risk factors. Other diagnostic group predictors include chromosomal abnormality, oncologic disease, acute diabetic complication, and nonoperative cardiovascular disease. Pre ICU risk factors include previous PICU admission for current hospitalization, pre ICU cardiopulmonary resuscitation, transfer from inpatient unit, and post operative status (within 24 hours). Other predictors include presence of cyanotic heart disease and presence of permanent or temporary cardiac pacing.

Additional examples of physiological data that may be used in determining risk of mortality include one or more physiological measurements such as a temperature measurement (e.g., continuous, periodic, and aperiodic), a heart rate measurement, a blood pressure measurement, a central venous pressure measurement, a pulsed oximetry measurement, a carbon dioxide concentration measurement, a respiratory rate measurement (e.g., respiratory plethysmograph, pulse oximetry, and end tidal carbon dioxide concentrations), an oxygen saturation measurement, and the like.

A variety of advanced organ specific monitoring devices or sensors for use in the PICU can be streamed to a bedside monitor and used as physiological data in systems and methods in accordance with the subject matter disclosed herein. Exemplary devices include: continuous cardiac output measurements (e.g., PICCO devices, available from Pulsion Medical Systems AG, of Munich, Germany, or Swan-Ganz catheter (available from Baxter Healthcare Corporation, of Deerfield, Ill.)); thoracic electrical bioimpedance continuous cardiac output (e.g., BIOZ® devices, available from Cardiodynamics International Corporation, of San Diego, Calif., and TEBCO® devices, available from Hemo Sapiens Inc., of Sedona, Ariz.); continuous in vivo arterial blood gas analysis (e.g., pH, PCO2, PO2, HCO3, base excess, and oxygen saturation analysis) (e.g., the VIA LVM monitor, available from Metracor Technologies, Inc., of San Diego, Calif.); continuous pulmonary mechanics and ventilator parameters (e.g., the Servo I device, available from Siemens AG, of Munich, Germany); continuous venous oxygen saturation measurement (e.g., devices available from Baxter Healthcare Corporation); continuous processed electroencephalographic analysis (e.g., the A2000 Bispectral Index monitoring system, Aspect Medical Systems Inc., of Natick, Me.), and continuous intracranial pressure measurements (CAMINO® ICP monitors, available from Camino Laboratories Inc., of San Diego, Calif.).

By use of one or more elements of physiological data, a real time, continuously updated risk of mortality score may be determined after analysis with a statistical model. The risk of mortality results may be displayed to a medical practitioner for use in patient treatment. Particularly, the results may be useful in treating PICU patients:

Evaluation of a Patient for Risk of Mortality

According to one aspect, a system for evaluating a patient in a PICU may be implemented as hardware, software, and/or firmware components executing on or with one or more modules of a patient monitoring system operable to collect physiological data. FIG. 1 is a diagram illustrating an exemplary patient monitoring system generally designated 100 for evaluating a patient in a PICU according to an embodiment of the subject matter described herein. System 100 may be any suitable system for collecting and analyzing physiological data. The physiological data may be in a digital format or any other suitable format for analysis by a computer system. System 100 may execute software suitable for collecting physiological data, storing the data, and analyzing the data for continually determining a risk of mortality of the patient.

System 100 may include a user interface 102 by which a user inputs data and information is presented to the user. For example, user interface 102 may include a keyboard 104 and a mouse 106 by which data and commands are input. Further, user interface may include any suitable input device such as a keypad, a touch screen interface or the like. The user can input commands into user interface 102 to initiate and manage collection of patient physiological data. User interface 102 may also include a display 108 for displaying information to the user. For example, display 108 may display collected physiological data and a risk of mortality of a patient. User interface 102 may also include one or more alarm indicators, such as a speaker or displayable icon, for indicating a predetermined level of the physiological data and/or a risk of mortality of the patient.

Further, system 100 may include a computer 110 having a physiological data store 112 configured for storing, at least temporarily, collected physiological data. Data store 112 may be a part of a memory of computer 110. The memory may include any suitable type of data storage in the form of devices, tapes, or disks. The memory may also include any suitable type of physical memory, such as computer chips capable of storing data. Physical memory can also include a computer's main memory or random-access memory (RAM), read-only memory (ROM), programmable read-only memory (PROM), erasable programmable read-only memory (EPROM), and electrically erasable programmable read-only memory (EEPROM). Computer 110 may include a processor configured for executing instructions stored in the memory and interfacing with user interface 102.

A data collector 114 may be hardware, software, and/or firmware components configured to collect physiological data associated with a patient upon admission to a PICU and at least once after admission to the PICU in accordance with the subject matter disclosed herein. The physiological data may be collected from one or more medical sensor units 116, each of which may be configured to sense or measure one or more physiological parameters of a patient. In response to sensing or measuring a physiological parameter, sensor unit 116 may generate an electrical signal representative of a physiological parameter and communicate the electrical signal to computer 110. The collected physiological data may be received and conditioned by computer 110 and stored in data store 112.

Additionally, the memory may store computer executable instructions configured for implementing the subject matter described herein. The subject matter described herein can be implemented as any suitable computer program product comprising computer executable instructions embodied in a computer readable medium. Exemplary computer readable media suitable for implementing the subject matter described herein include disk memory devices, chip memory devices, application specific integrated circuits, programmable logic devices, and downloadable electrical signals. In addition, a computer program product that implements the subject matter described herein may be located on a single device or computing platform. Alternatively, the subject matter described herein can be implemented on a computer program product that is distributed across multiple devices or computing platforms.

A mortality risk function 118 may include computer executable instructions for analyzing physiological data associated with a patient with a statistical model and continually determining a risk of mortality of the patient. Function 118 may receive collected physiological data from data store 112 and analyze the data with a statistical model as disclosed herein: Based on the analysis, a risk of mortality of the patient may be determined. For example, the risk of mortality may be determined at admittance of the patient to PICU and continually following admittance. The risk may be updated post-treatment so that the effects of the treatment on the risk of mortality can be analyzed. The analysis may result in a mortality risk score that may be displayed via display 108. A medical practitioner may use the displayed risk of mortality for evaluating the clinical status of the patient and tracking the patient's response to a wide range of interventions. The score or other indicator of risk may be used for other purposes, such as PICU staffing or bed assignment. For example, a patient with a risk of mortality that exceeds a threshold may be assigned additional staff for more frequent monitoring and/or treatment.

Figure 2:
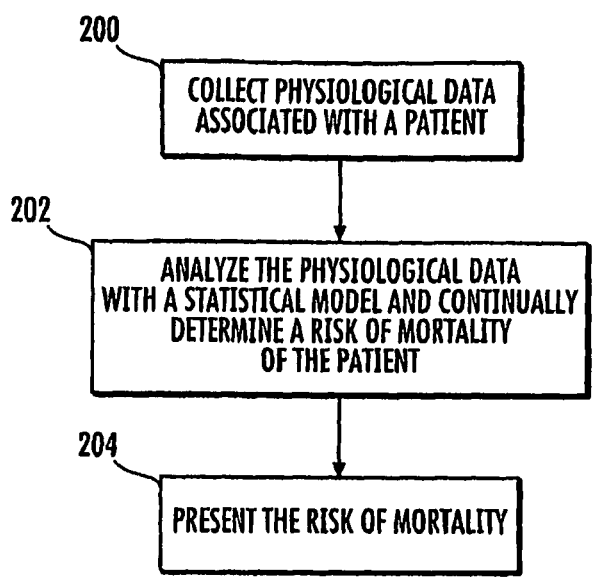
FIG. 2 is a flow chart of an exemplary process for evaluating a patient in a PICU in accordance with an embodiment of the subject matter described herein.

FIG. 2 is a flow chart illustrating an exemplary process for evaluating a patient in a PICU in accordance with an embodiment of the subject matter described herein. This exemplary process is described with reference to system 100 shown in FIG. 1. Referring to FIGS. 1 and 2, in block 200, physiological data associated with a patient is collected. The data may be collected upon admission of the patient to the PICU and continuously or at one or more intervals after admission to the PICU. Initial demographic and observational data may be collected when the patient is admitted. Further, the demographic and observational data may be input to computer 110 by user interface 102, file transfer, and any other suitable technique. The physiological data may initially be collected in raw form and later recoded into multiple optimized derogatory indicators for use in assessing the patient's risk of mortality. The data may be stored in data store 112.

Continuous digital data streams carrying continuous physiological signals may be written by data collector 114 to data store 112 in an SQL database structure. For example, streams of physiological data may be received from sensing units 116. The signals may be written at regular intervals, such as every 8 seconds. The stored data may include information detailing which patient the data is streaming from, UTC time stamps, and individual physiological data elements. SQL commands may be written to copy this stored data to a research SQL database via a direct network connection.

In an example of collecting physiological data, ECG signals may be captured at bedside and streamed into a data file of data store 112. For example, ECG signals may be acquired in an analog format on an ULTRAVIEW® 1700 monitor (available from Spacelabs Healthcare, Inc., of Issaquah, Wash.) and sampled at 896 Hz. The digitized signal may be down sampled and stored at 224 Hz in an SQL database with a UTC time stamp and patient ID number. An anti-aliasing filter may be used for minimizing signal distortion.

Figure 3:
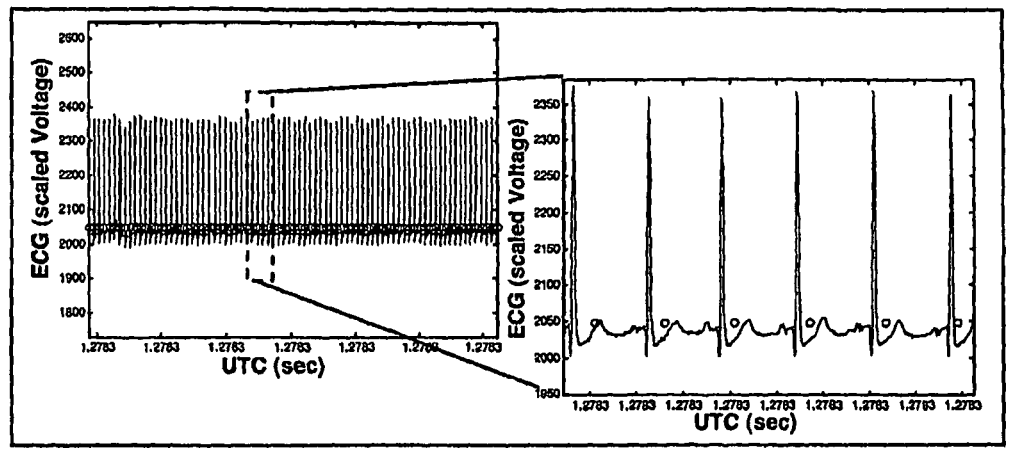
FIG. 3 is a graph of an example of an ECG signal with approximations of a fiducial point obtained by a monitoring system according to an embodiment of the subject matter described herein.
Figure 4:
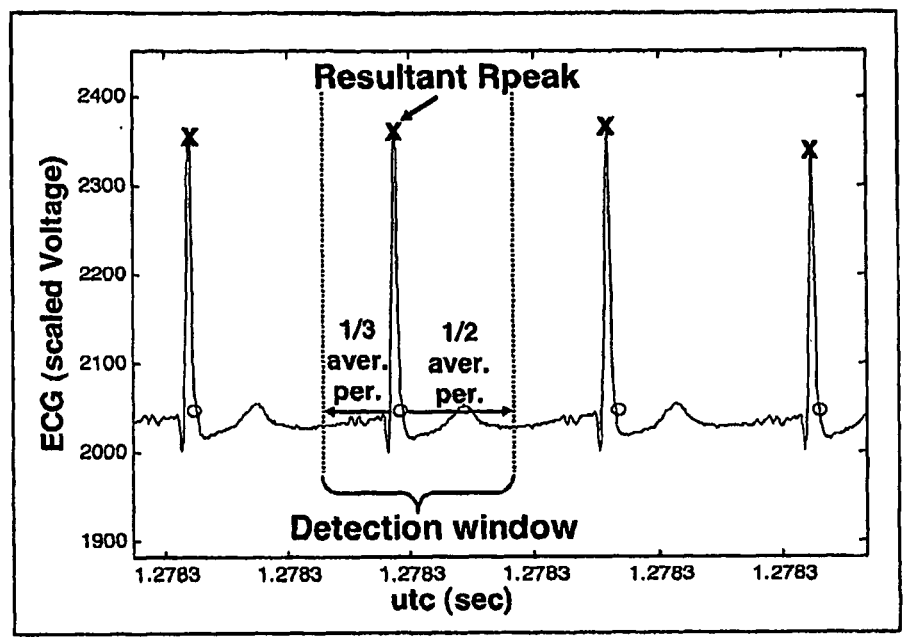
FIG. 4 is a graph of an R wave of an ECG signal.

FIG. 3 is a graph illustrating an example of an ECG signal with approximations of a fiducial point (R wave (tall peak)) obtained by a monitoring system. An algorithm may be applied to the signal for detecting the exact location of the fiducial point from which the RR interval (i.e., time between R peaks), heart period, and heart rate time series are derived. FIG. 4 is a graph illustrating an R wave of an ECG signal. From generated vicinity marks, the exact R wave may be detected. Further, the R-R interval may be measured to generate a heart period time series for use in determining a risk of mortality.

ECG signal data may be processed for identification of peaks within the signal flow. For example, the signal data may be processed by a suitable software package such as MATLAB® software available from The MathWorks, Inc., of Natick, Me. Spectral-dimensions may be calculated using a voltage reading associated with a time stamp. A data file may be created from the identified signal flow peaks and the calculated spectral-dimensions. The data file follows a multi-hierarchical structure. Sets of time domain variables and frequency domain variables may be generated and uniquely stored in data store 112. The time domain variables identify the peak of each beat and its exact time. Frequency domain variables use beats per minute units.

Time-domain based transformations may be generated by sizing the lag between contiguous heart peaks and aggregating them into percents within tenth-of-a-second groups. Streaming heart peak information may be lagged and new transformed variables created by binning their time differences. First and second derivatives may be calculated and trended for indicating condition change. Using R-R interval data, the following data may be calculated: standard deviation of the consecutive normal sinus intervals (SDNN), root mean square successive difference (RMSSD), number of NN intervals with differences greater than 50 ms (NN50), the proportion of NN50 intervals divided by the total NN intervals (pNN50), pNNx series (where x=time>0 ms), NN range, coefficient variation, and the minimum/maximum heart period for each 128 beat minor time epoch.

The following software code provides an example of sizing the lag between contiguous heart peaks and aggregating them into percents within tenth-of-a-second groups. The variable "nn_interval" represents the lag time between continuous heart peaks. In the code, 12 new transformed variables are created by binning their time differences.

nn_interval=rpeaktime_stamp-lag1(rpeaktime_stamp);
if nn_interval >0 and nn_interval <=0.05 then NN50=1;
if nn_interval >0.05 and nn_interval <=0.10 then NN100=1;
if nn_interval >0.10 and nn_interval <=0.20 then NN200=1;
if nn_interval >0.20 and nn_interval <=0.30 then NN300=1;
if nn_interval >0.30 and nn_interval <=0.40 then NN400=1;
if nn_interval >0.40 and nn_interval <=0.50 then NN500=1;
if nn_interval >0.50 and nn_interval <=0.60 then NN600=1;
if nn_interval >0.60 and nn_interval <=0.70 then NN700=1;
if nn_interval >0.70 and nn_interval <=0.80 then NN800=1;
if nn_interval >0.80 and nn_interval <=0.90 then NN900=1;
if nn_interval >0.90 and nn_interval <=1.0 then NN1000=1;
if nn_interval >1.0 and nn_interval <=3.0 then NN1000P=1;

Frequency-domain transformations may be generated by grouping bands of frequencies and by calculating ratios and variance terms within the bands. The following software code provides an example of grouping bands of frequencies and by calculating ratios and variance terms within the bands. The variable "frequency" represents heart rate frequency, the variable "1-ULF" represents ultra low frequency, the variable "2-VLF" represents very low frequency, the variable "2-LF" represents low frequency, and the variable "4-HP" represents high frequency. Other suitable non-linear transformations may be used.

freq_type='';
if frequency >=0 and frequency <=0.003 then freq_type='1-ULF';
if frequency >=0.0031 and frequency <=0.040000 then freq_type='2-VLF';
if frequency >=0.040001 and frequency <=0.150 then freq_type='3-LF';
if frequency >=0.150001 then freq_type='4-HF';
if freq_type='' then delete;
constant=(1/(128*2));
if frequency=1 then
heart_rate_spectra_inter=(((heart_rate_spectra_inter)*2)+constant);
if frequency >0 then
heart_rate_spectra_inter=(((heart_rate_spectra_inter)*2)+(constant*2)); run;

As shown in this code, two calculated variables, "frequency" and "heart_rate_spectra_inter," may be grouped into four frequency bands. In particular, frequency may be grouped into one of 1-ULF, 2-VLF, 3-LF, and 4-HF. Another variable can include low frequency divided by high frequency (LF/HF). Typical values for the LF/HF power ratio are greater than 1 for normal resting state and may increase to much larger values when sympathetic activity increases (e.g., during standing or exercise). A lowered ratio of LF activity to HF activity is typically associated with critical illness.

Figure 5:
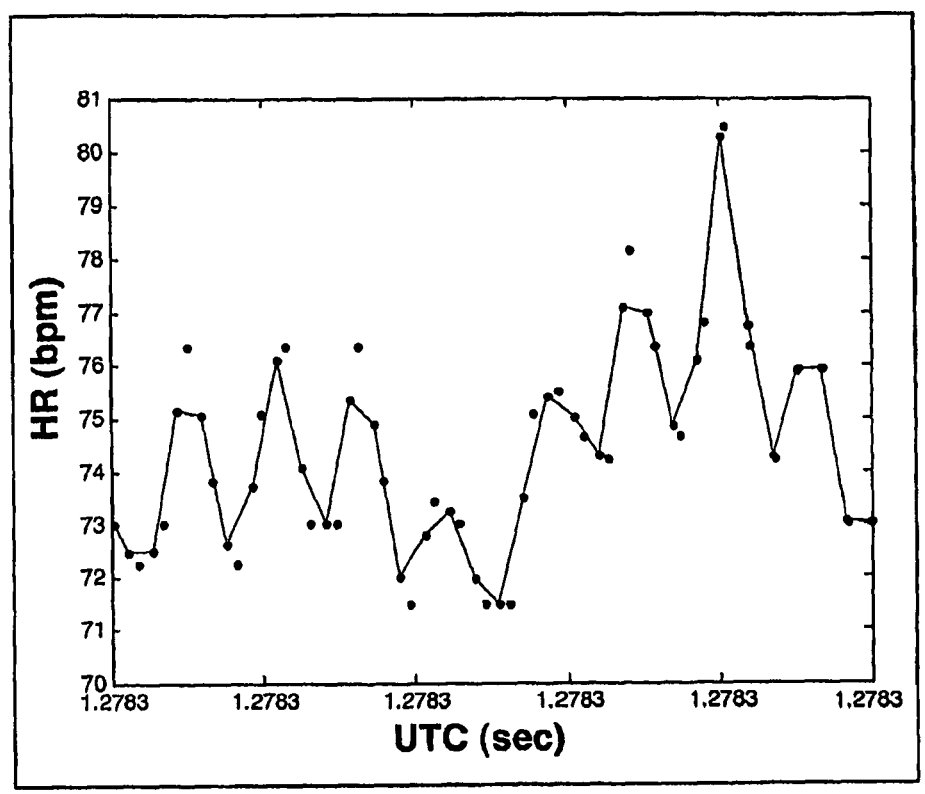
FIG. 5 is a graph of an example of sample interpolations of heart rate data points.

Heart rate time series may be interpolated to achieve a uniform sampling interval. FIG. 5 is a graph illustrating an example of sample interpolations of heart rate data points. The interpolated heart rate data set is normalized to mean zero and variation from the mean, such that direct comparison of variation of heart rate, irrespective of mean heart rate, may be made between patients, as well as within a patient over time.

Figure 6:
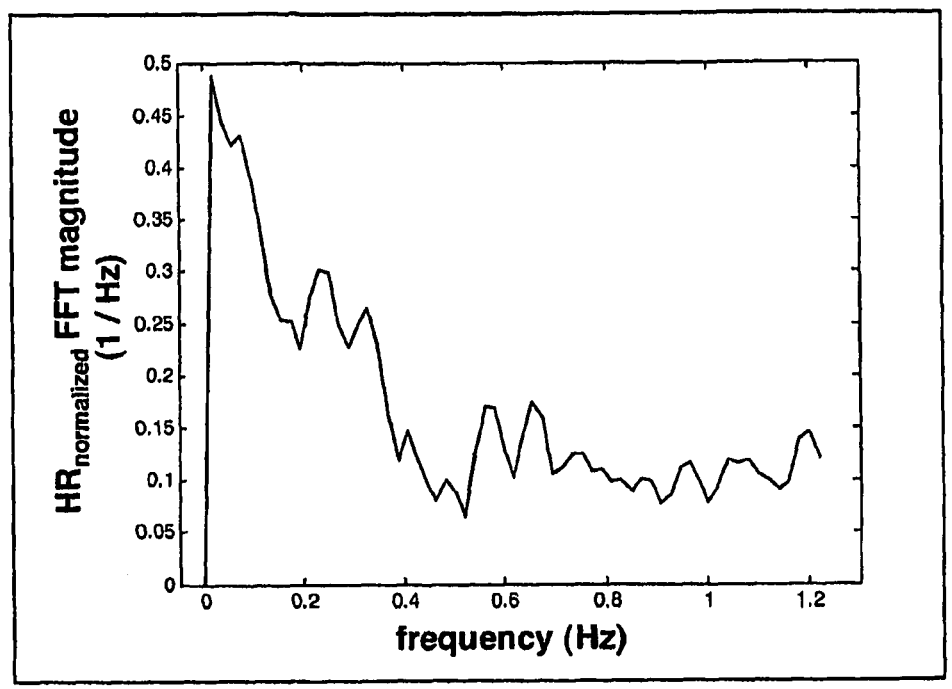
FIG. 6 is a graph illustrating an example of heart rate FFT magnitude spectrum averaged from 12 individual 128 beat segments.

An amplitude spectrum may be generated using the fast Fourier transform (FFT) to display the spectral bands which characterize autonomic activity and other physiological mechanisms involved in heart rate control. The amplitude spectrum may be used for determining a risk of mortality in accordance with the subject matter disclosed herein. FIG. 6 is a graph illustrating an example of heart rate FFT magnitude spectrum averaged from 12 individual 128 beat segments. The power spectrum derived from the amplitude spectra may be used to determine frequency band specific variance of the heart rate time series for statistical tests of significance for equal variance of a specific band. Sequential records of power spectra may be generated once every 128 beats (approximately every 1-2 minutes in children). From each spectrum, frequency bands may be integrated to generate a parameter for each band proportional to the variance in the time-domain data which contributes to the band. The frequency bands include ultra low frequency (ULF) of about 0 to 0.003 Hz, very low frequency (VLF) of about 0.003 to 0.04 Hz, low frequency (LF) of about 0.04 to 0.15 Hz, and high frequency (HF) of greater than about 0.15 Hz. The generated data is available for further ratio analysis, which have been shown to be sensitive to changes in the underlying processes governing heart rate (e.g., level of sympathetic and parasympathetic activity).

The sequential spectrograms may be presented progressively with time such that power versus frequency as a function of time is visualized. Power ratios may also be processed as a time function. The results of the data processing may be formatted in an open database connectivity (ODBC) compliant database for data storage and subsequent integration with the statistical and neural network software. The output data includes a universal time code (UTC) time tag, frequency and power level values. Test signals with known spectral content may be used to validate the signal processing techniques used in heart rate variability analyses.

Statistical analyses in the time domain and/or the frequency domain may be applied to any physiological signal that is acquired in a time-continuous manner. Any one or more of such physiological signals can be analyzed in a similar manner described above with respect to ECG signals for use in application to a statistical model for predicting a risk of mortality.

Systemic blood arterial pressure (SAP) is an example of a time-continuous physiological signal. SAP is predominantly regulated through the carotid arch and carotid sinus baroreceptor reflexes with efferent influence on the sinus and atrioventricular nodes via the cardiac nerves. This reflex control mechanism has a time constant of approximately 10 seconds with a frequency band of interest in the region of 0.1 Hz. SAP variability may be determined from a time series of peak pressure points in the invasive blood pressure waveform. Dynamic SAP may be associated with heart rate variability (HRV) at the LF band, the HF band, and/or the VLF band. The pressure variability time series (PV) may be generated as the inverse of peak pressure period. As with the HRV series, the PV may be normalized by mean rate and the deviation from the mean to generate the normalized PV time series for spectral analysis. Cross spectral analysis between HRV and PV may be performed in the vicinity of the LF, the VLF, and/or the HF bands to uncover activity between these two interacting signals.

Another example of a time-continuous physiological signal that may be used in determining a PICU patients risk of mortality is respiratory rate. A consistent marker in the respiratory cycle (onset of respiration) may be detected in a set of patients with the end tidal $CO_2$ monitor and from the respiratory plethysmograph. The respiratory period may be converted to respiratory rate, interpolated to a constant sample interval, normalized and respiratory rate variability analyzed. Cross spectral analysis of the respiratory spectrum with the heart rate spectrum is highly correlated (high coherence) at the respiratory frequency (0.2 to 0.3 Hz in adults) in healthy patients. A fall in cross spectral power or a diminished coherence between these spectra may indicate a progression of disease state, thus it may be used as a predictor of a risk of mortality. The cross spectral band of interest may be established from the mean respiratory rate and variance in children.

Laboratory tests may be administered and the results may be entered into system 100 for use in determining a risk of mortality. Exemplary laboratory tests include the following: cardiac such as oscillometric blood pressure and lactate level (hourly systolic and diastolic); respiratory such as arterial blood gas determination (pH, $PCO_2$, $PO_2$, $HCO_3$, and calculated $O_2$ saturation) and fractional inspired oxygen concentration (hourly); neurologic such as Glasgow coma score (hourly) and papillary reactions (equal and/or reactive) (hourly); fluid, electrolytes, and renal function such as levels of sodium, potassium, glucose, urea nitrogen, creatinine concentrations, ionized calcium, whole blood glucose measurements (Dextrostick), and urine output (hourly); hematologic such as hemoglobin, platelet count, prothrombin time INR, partial thromboplastin time, and D-dimers; hepatic such as bilirubin (total, direct, and indirect), transaminases (AST and ALT), albumin, and total protein); and immunologic such as temperature (hourly if not captured continuously), white cell count (total) absolute neutrophil count, absolute lymphocyte count, and c reactive protein.

In one experiment, laboratory tests were administered to 10 patients. Table 1 below shows results of tests that were obtained at different intervals.

TABLE 1

Laboratory Test Results

| Short Name | Frequency | Percentage |
|---|---|---|
| ALT | 61 | 0.7382 |
| APTT | 128 | 1.5491 |
| AST | 62 | 0.7503 |
| Albumin | 52 | 0.6293 |
| BUN | 184 | 2.2268 |
| BaseBal | 493 | 5.9664 |
| Bicarb | 433 | 5.2402 |
| Bili-total | 74 | 0.8956 |
| Bili-unconj | 6 | 0.0726 |
| Bili-conj | 8 | 0.0968 |
| CRP | 6 | 0.0726 |
| Calcium | 496 | 6.0027 |
| Creatine Kinase | 6 | 0.0726 |
| Creatinine | 201 | 2.4325 |
| D Dimers | 6 | 0.0726 |
| Glucose | 666 | 8.0600 |
| HCT | 243 | 2.9408 |
| HGB | 612 | 7.4065 |
| INR | 121 | 1.4644 |
| Lactate | 452 | 5.4702 |
| Lymphabs | 66 | 0.7987 |
| O2Sat | 431 | 5.2160 |
| PCO2 | 489 | 5.9179 |
| PCO2-ven | 10 | 0.1210 |
| PH | 489 | 5.9179 |
| PH-ven | 10 | 0.1210 |
| PO2 | 488 | 5.9058 |
| PO2-ven | 10 | 0.1210 |
| PT | 98 | 1.1860 |
| Platelet | 199 | 2.4083 |
| Potassium | 675 | 8.1689 |
| Sodium | 702 | 8.4957 |
| Tprotein | 9 | 0.1089 |
| Troponin | 11 | 0.1331 |
| WBC | 199 | 2.4083 |
| neutroabs | 67 | 0.8108 |
| | 8263 | 100.0000 |

Each test was processed using Quantitative Target Modeling System (QTMS) (available from SAS Institute Inc., of Cary, N.C.), which binned the total distribution into deciles identifying "significant intervals" within each variable which demonstrates higher than or lower than mortality rates when compared to the total. Once accomplished, selecting indexes greater than 120 resulted in Table 2 below.

TABLE 2

Mortality Index

| Obs | Title | Interval | Mortality |
|---|---|---|---|
| 1 | ALT | 34-47 | 130 |
| 2 | ALT | 142-365 | 130 |
| 3 | APTT | 39.5-41.9 | 125 |
| 4 | APTT | 42.2-45.1 | 125 |
| 5 | AST | 167-347 | 129 |
| 6 | AST | 835-1841 | 129 |
| 7 | ALBUMIN | 1.5-1.6 | 141 |
| 8 | ALBUMIN | 3.1-3.4 | 141 |
| 9 | BUN | 78-107 | 188 |
| 10 | BILI_TOT | 4.6-8.5 | 130 |
| 11 | BILI_TOT | 37.8-40 | 130 |
| 12 | BILI_TOT | 40.5-42.6 | 130 |
| 13 | BILI_TOT | 43.5-47.9 | 130 |
| 14 | BILI_UN | 11.2 | 200 |
| 15 | BILI_UN | 11.3 | 200 |
| 16 | BILI_CON | 0.7 | 200 |
| 17 | BILI_CON | 0.9 | 200 |
| 18 | CALCIUM | 5.53-16.23 | 147 |
| 19 | CREATKIN | 66 | 150 |
| 20 | CREATKIN | 103 | 150 |
| 21 | CREATKIN | 132 | 150 |
| 22 | CREATKIN | 2416 | 150 |
| 23 | CREATINE | 1.4-2.4 | 183 |
| 24 | CREATINE | 2.7-3.8 | 183 |
| 25 | DDIMER | . | 600 |
| 26 | HCT | 46-52.8 | 166 |
| 27 | INR | 2-2.2 | 122 |
| 28 | INR | 2.3-3.6 | 122 |
| 29 | LACTATE | 7.4-12.4 | 147 |
| 30 | LACTATE | 12.5-23 | 147 |
| 31 | LYMPHABS | 7.5 | 200 |
| 32 | PT | 8.7-10.5 | 129 |
| 33 | PT | 29-51.5 | 129 |
| 34 | PLATELET | 18-60 | 154 |
| 35 | PLATELET | 61-75 | 154 |
| 36 | PLATELET | 76-89 | 154 |
| 37 | PLATELET | 90-107 | 154 |
| 38 | PLATELET | 108-131 | 154 |
| 39 | SODIUM | 150-157 | 153 |
| 40 | SODIUM | 158-165 | 153 |
| 41 | TPROTEIN | 4.4 | 225 |
| 42 | TPROTEIN | 7.9 | 225 |
| 43 | TPROTEIN | 8.1 | 225 |

TABLE 2-continued

Mortality Index

| Obs | Title | Interval | Mortality |
|---|---|---|---|
| 44 | TPROTEIN | 0.029 | 550 |
| 45 | O2SAT | 76.3-84.9 | 148 |
| 46 | HGB | 15.2-19.2 | 148 |
| 47 | PO2 | 42-48 | 144 |
| 48 | LACTATE | 4.4-7.3 | 141 |
| 49 | PLATELET | 133-165 | 147 |
| 50 | PO2 | 16-36 | 141 |
| 51 | BASEBAL | −11.1 | 140 |
| 52 | BASEBAL | −3 | 140 |
| 53 | BICARB | 10.5-17.5 | 149 |
| 54 | PH | 6.91-7.25 | 137 |
| 55 | SODIUM | 144-149 | 140 |
| 56 | BICARB | 17.7-20.2 | 146 |
| 57 | HCT | . | 150 |
| 58 | HGB | 13.7-15.1 | 135 |
| 59 | O2SAT | 37.4-68.8 | 134 |
| 60 | LYMPHABS | 3.2-6.1 | 175 |
| 61 | BUN | 33-48 | 161 |
| 62 | PO2 | 37-41 | 128 |
| 63 | NEUTROAB | 8.7-10.3 | 169 |
| 64 | PH | 7.33-7.34 | 126 |
| 65 | CALCIUM | 5.25-5.51 | 125 |
| 66 | WBC | 21.7-31.8 | 131 |
| 67 | PH | 7.26-7.32 | 126 |
| 68 | BICARB | 20.3-21.3 | 134 |
| 69 | O2SAT | 68.9-76.1 | 127 |
| 70 | BASEBAL | −1.4 | 124 |
| 71 | CREATINE | 1-1.1 | 151 |
| 72 | CALCIUM | . | 120 |
| 73 | WBC | 11.6-12.3 | 126 |
| 74 | O2SAT | 99.8-100 | 123 |
| 75 | CREATINE | 1.2-1.3 | 148 |
| 76 | PCO2 | 20-34 | 121 |
| 77 | WBC | 17.1-20.9 | 123 |
| 78 | HGB | 6.2-8.6 | 121 |
| 79 | GLUCOSE | 83-91 | 121 |
| 80 | HCT | 41.2-45.6 | 126 |
| 81 | CREATINE | 0.4 | 136 |
| 82 | HCT | 38.2-41 | 122 |
| 83 | LYMPHABS | 1.7-2.1 | 143 |
| 84 | NEUTROAB | 10.8-11.4 | 141 |
| 85 | NEUTROAB | 11.6-13.6 | 141 |
| 86 | BUN | 49-73 | 122 |
| 87 | LYMPHABS | 1.4-1.6 | 125 |
| 88 | TROPONIN | 0.063-0.088 | 275 |

Table 3 below shows 95 intervals that assist in excluding a predicted fatal outcome.

TABLE 3

Mortality Predictors

| Obs | Title | Interval | Mortality |
|---|---|---|---|
| 1 | INR | 1.4 | 79 |
| 2 | INR | 1.5-1.6 | 77 |
| 3 | PT | 16-16.8 | 77 |
| 4 | PT | 18.5-19.9 | 77 |
| 5 | BILI_TOT | 0.3-0.9 | 74 |
| 6 | APTT | 25.1-28.6 | 68 |
| 7 | APTT | 29.4-34.5 | 68 |
| 8 | LACTATE | 1.6-1.9 | 78 |
| 9 | BASEBAL | 7.9-14.2 | 78 |
| 10 | SODIUM | 1.6-1.9 | 80 |
| 11 | PO2 | 137-138 | 76 |
| 12 | AST | 42-56 | 65 |
| 13 | ALBUMIN | 2.6-2.7 | 70 |
| 14 | ALBUMIN | 3.8 | 70 |
| 15 | BASEBAL | −2 | 75 |
| 16 | CALCIUM | 4.58-4.75 | 73 |
| 17 | O2SAT | 97.6-98.2 | 74 |
| 18 | HCT | 18.4-28.4 | 80 |
| 19 | HGB | 10-10.5 | 71 |
| 20 | GLUCOSE | 111-119 | 73 |
| 21 | HGB | 9.4-9.9 | 70 |
| 22 | PO2 | 109-127 | 69 |
| 23 | LACTATE | 1-1.2 | 67 |
| 24 | BASEBAL | 5.3-7.8 | 67 |
| 25 | BICARB | 24.2-25.5 | 72 |
| 26 | PH | 7.41-7.43 | 66 |
| 27 | ALBUMIN | 2.2.-2.5 | 60 |
| 28 | CREATINE | 0.7-0.9 | 78 |
| 29 | HGB | 10.6-11.3 | 65 |
| 30 | CALCIUM | 4.34-4.57 | 63 |
| 31 | O2SAT | 98.8-99.2 | 62 |
| 32 | SODIUM | 121-134 | 63 |
| 33 | BICARB | 26.9-29.1 | 66 |
| 34 | BUN | 19-30 | 75 |
| 35 | BICARB | 29.2-32.1 | 61 |
| 36 | SODIUM | 139-140 | 56 |
| 37 | O2SAT | 94.4-97.5 | 55 |
| 38 | HCT | 30.6-32 | 58 |
| 39 | HCT | 32.1-34.2 | 58 |
| 40 | LACTATE | 0.3-0.9 | 51 |
| 41 | ALT | 24-32 | 43 |
| 42 | AST | 18-41 | 43 |
| 43 | BILI_TOT | 1-1.4 | 43 |
| 44 | NEUTROAB | 4.6-5.7 | 66 |
| 45 | NEUTROAB | 5.9-6.7 | 66 |
| 46 | WBC | 2.8-6.9 | 49 |
| 47 | PLATELET | 167-212 | 46 |
| 48 | BUN | 10-Aug | 55 |
| 49 | NEUTROAB | 1.8-4.5 | 56 |
| 50 | NEUTROAB | 7.1-7.4 | 56 |
| 51 | CREATINE | 0.5 | 48 |
| 52 | BUN | . | 47 |
| 53 | SODIUM | . | 38 |
| 54 | PO2 | 68-89 | 36 |
| 55 | LYMPHABS | 1-1.3 | 44 |
| 56 | GLUCOSE | . | 31 |
| 57 | HCT | 28.5-30.5 | 29 |
| 58 | BUN | 5-Feb | 28 |
| 59 | PLATELET | 216-316 | 23 |
| 60 | CREATINE | 0.6 | 20 |
| 61 | LYMPHABS | 318-441 | 20 |
| 62 | CREATINE | . | 14 |
| 63 | PLATELET | 318-441 | 8 |
| 64 | BILI_UN | 12.8 | 0 |
| 65 | BILI_UN | 13.7 | 0 |
| 66 | BILI_CON | 0.1 | 0 |
| 67 | BILI_CON | 0.2 | 0 |
| 68 | CRP | . | |
| 69 | CRP | 1.4 | 0 |
| 70 | CRP | 6.3 | 0 |
| 71 | CRP | 14.7 | 0 |
| 72 | CRP | 15.5 | 0 |
| 73 | CREATKIN | 49 | 0 |
| 74 | CREATKIN | 53 | 0 |
| 75 | DDIMER | 375 | 0 |
| 76 | DDIMER | 445 | 0 |
| 77 | DDIMER | 471 | 0 |
| 78 | DDIMER | 1565 | 0 |
| 79 | DDIMER | 1718 | 0 |
| 80 | PCO2_VEN | 51 | 0 |
| 81 | PH_VEN | 7.31 | 0 |
| 82 | PO2_VEN | 43 | 0 |
| 83 | PLATELET | 447-913 | 0 |
| 84 | TPROTEIN | . | 0 |
| 85 | TPROTEIN | 5.1 | 0 |
| 86 | TPROTEIN | 6.1 | 0 |
| 87 | TPROTEIN | 7.7 | 0 |
| 88 | TPROPONIN | . | 0 |
| 89 | TPROPONIN | 0.033 | 0 |
| 90 | TPROPONIN | 0.035 | 0 |
| 91 | TPROPONIN | 0.036 | 0 |
| 92 | TPROPONIN | 0.045 | 0 |
| 93 | TPROPONIN | 0.05 | 0 |

TABLE 3-continued

Mortality Predictors

| Obs | Title | Interval | Mortality |
|---|---|---|---|
| 94 | TPROPONIN | 0.056 | 0 |
| 95 | TPROPONIN | 0.058 | 0 |

The exemplary mortality index and predictors shown in Tables 2 and 3 above may be utilized in a statistical model for determining a risk of mortality of a patient in accordance with the subject matter disclosed herein. The mortality column in the tables provides a weight associated with the corresponding row. The weight assigns the level at which the associated physiological variable impacts the risk of mortality of the patient.

Figure 9:
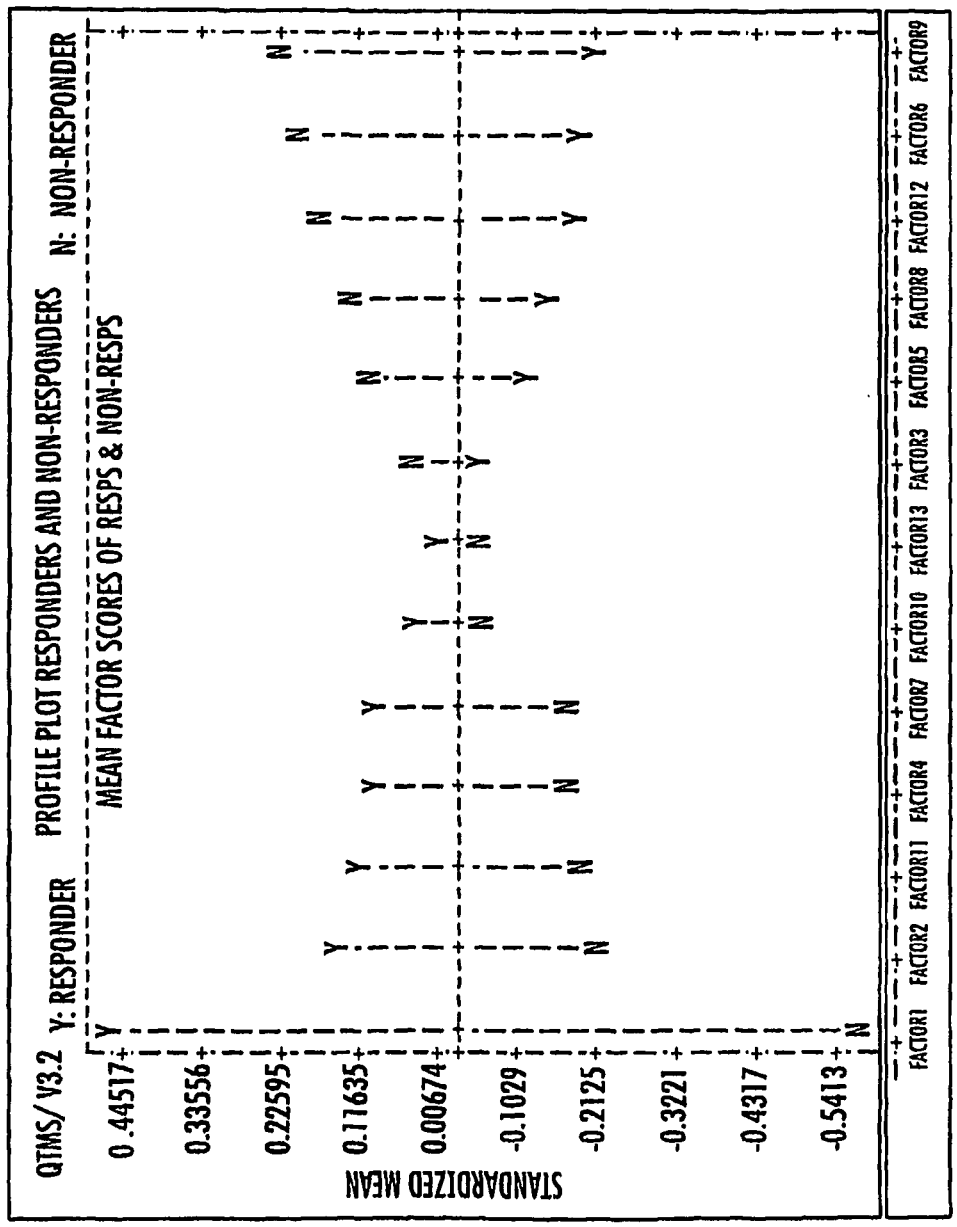
FIG. 9 is a graphical representation of the ability of the factors as a standardized difference between Y and N outcome groups.

Patient chart data may be used in the statistical model described herein for determining the risk of mortality of a patient. Upon admittance, one or more raw variables may be collected from chart data. For example, FIG. 7 is a chart illustrating 22 significant intervals obtained from 11 raw variables in accordance with an embodiment of the subject matter disclosed herein. These candidate intervals may be recorded as new binary variables labeled with an appropriate range that identifies it as a significant interval. Next, this list may be "orthogonalized" using an anchored factor analysis. The results are shown in the chart illustrated in FIG. 8. The result includes 13 factors explaining 83% of the variance. These factors were analyzed for identifying the factors according to their ability to differentiate between dead and live patients. FIG. 9 is a graphical representation showing the ability of the factors as a standardized difference between Y and N outcome groups. This data may be used in a statistical model for determining a risk of mortality of a patient.

Physiological data may be collected at different rates. For example, ECG data may be collected at millisecond intervals and processed into time domain information at subsecond intervals. Frequency domain information may be collected in increments that vary about 128 beats and then interpolated into strict 128 beats that vary along an approximate one minute interval. Laboratory and chart information may be collected repeatedly as requested. Demographic information may be collected once at admittance. A common time frame is required to join this information. The information may be taken and different time intervals and re-aggregated into strict fixed time intervals. In one example, a two minute time frame may be used, although any other suitable time frame may be used.

Once all data is re-aggregated into two minute increments, first and second derivatives may be calculated and monitored for trending and changes. After each of the resultant files are calibrated into two minute packages of equal intervals, the files may be merged to identify common collection time frames across all information. Trending and change information may be used in a statistical model for determining a risk of mortality of the patient.

Referring to FIGS. 1 and 2, at block 202, the physiological data is analyzed with a statistical model and a risk of mortality continually determined. A statistical model may include a scoring algorithm containing a checklist of known derogatory indicators. The derogatory indicators may be constantly updated and fed into computer 110. In one example, the data may be sourced from a real-time stream of information coming from an ECG monitor. Every 128 beats may produce a set of frequency data. The data is aggregated into intervals along with the time difference percentages flowing out from the time domain sourced data. The packets may then be scored and a predicted segment-outcome calculated. The predicted outcome may be accumulated over the first four hours of admittance. Based upon the dominance of the predicted outcome, a clinical classification may be made. The classification may be monitored for changes over time. The risk of mortality may be represented by a risk of mortality score, which is continually updated for real-time monitoring of the risk of mortality. In one example of presenting data, the risk of mortality and physiological data may each be classified by color, where green represents a normal condition, yellow represents an unstable condition, and red represents a not normal condition.

In one example of model building, the SAS® Enterprise Miner™ 5.1 and Quantitative Target Modeling System (QTMS) (available from SAS Institute Inc.) may be used for statistical model building. In this example, the following different classes of input variables are used: real time continuous physiological signals, advanced measures of heart rate variability, physiological based indices of organ function and their variability, demographic and diagnosis related predictors of mortality. These variables may be transformed and composite variables generated. The variables may be scanned and summarized via a multivariate algorithm of QTMS for calculating a variety of statistics for each variable including lift from base, t-tests, chi-square analysis, indices, missing data, and confidence intervals. Significant intervals within each variable are selected depending on a specified lift from base criteria. Binary recoding of individual intervals found within each predictor can then be performed.

A statistical model may be developed by examining the covariation of all variables in response to a primary outcome (e.g., death versus survival). After each variable is scanned, a summary sheet is produced that rank orders all high/low intervals. These variables are factor analyzed to organize a selection of orthogonal explanation variables and then rank ordered according to their ability to differentiate between the target definitions. This process investigates a large pool of potential independent variables, identifies significant intervals within each variable distribution, reduces the pool into orthogonal factors, introduces pre-screened variables into a multivariate scoring technique, and calculates the performance of the model on both the estimation sample and hold out validation samples. Exemplary statistical models include a linear regression model, an autoneural network model, a logistic regression model, a DMneural model, a decision tree model, a neural network model, a minimum Bayes-risk (MBR) model, and a rule induction model.

At block 204, the risk of mortality may be presented via user interface 102. For example, the risk of mortality may be a value displayed as a number or graphically on display 108. Further, the physiological data such as the variables used for determining the risk of mortality may be presented via user interface 102. Variables may be displayed as being within a normal range (adjusting for age, sex, and diagnosis) or derogatory. A time series analysis of each variable, including the first and second derivative of the variable may be presented. Drill downs may also be presented by user selection.

Experimentation

In one experiment, a sample of twenty-eight pediatric patients, matched on age, sex, and diagnosis, from a PICU was selected as an analytic set for providing proof of concept principles of the subject matter disclosed herein. The experiment differentiated between children who die (14 of the patients) from those matched survivors (14 of the patients) using the following four classes of variables: real time continuous physiological signals (i.e., heart rate); advanced measures of variability of the physiological signals (i.e., spectral analysis); physiological based measures of organ function (i.e., serum glucose) and their variability; and demographic (i.e., age) and diagnosis related (i.e., post operative status) predictors of pediatric mortality. Since this experiment is a case control analysis, the mortality rate from this sample is 50%.

Figure 10A:
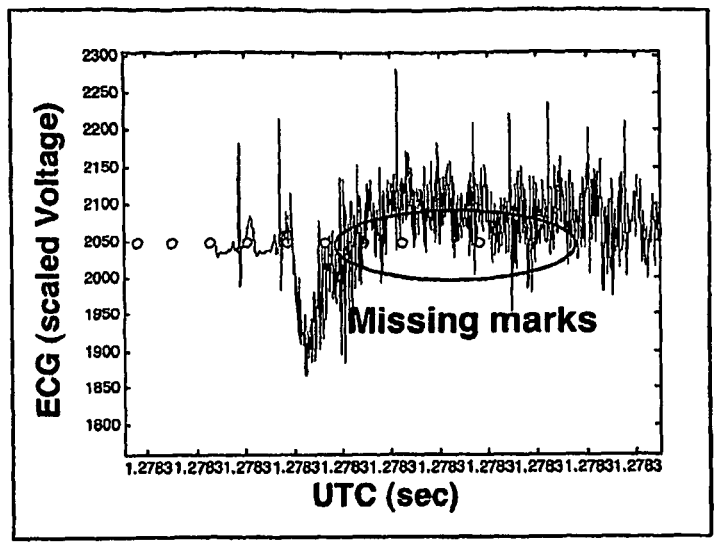
FIGS. 10A and 10B are graphs of an unfiltered ECG signals with an R peak estimation.
Figure 10B:
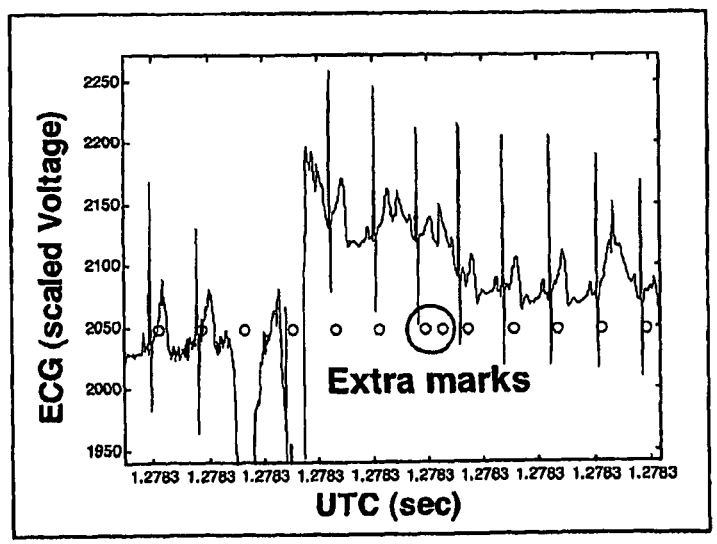

Streaming ECG data was captured at 224 data points per second tagged with a UTC millisecond time stamp provided by an ICU monitoring system. The R peaks of the ECG signal were estimated by an analog process and improved upon by an algorithm which identified and corrected errors and artifacts using a running average technique. FIGS. 10A and 10B are graphs illustrating an unfiltered ECG signals with an R peak estimation.

Figure 11A:
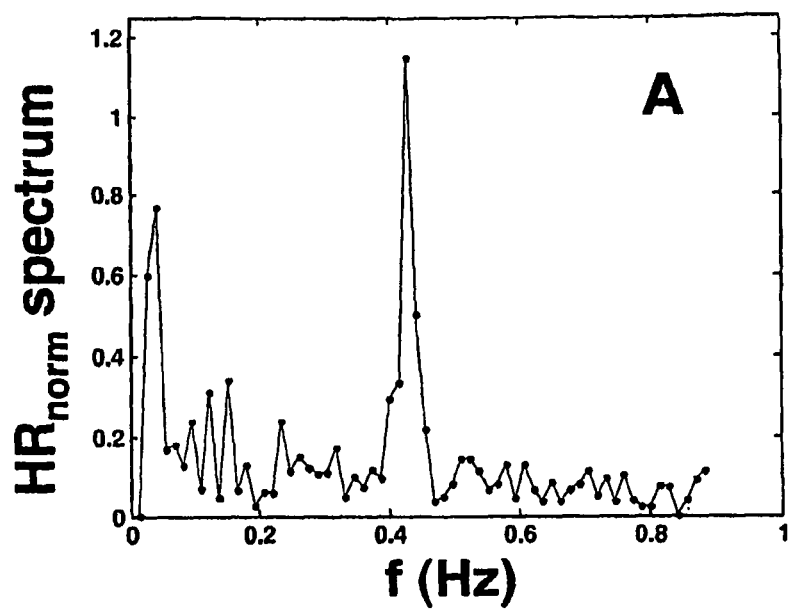
FIGS. 11A and 11B are graphs of heart rate spectral curves for a surviving child and a child who died, respectively.
Figure 11B:
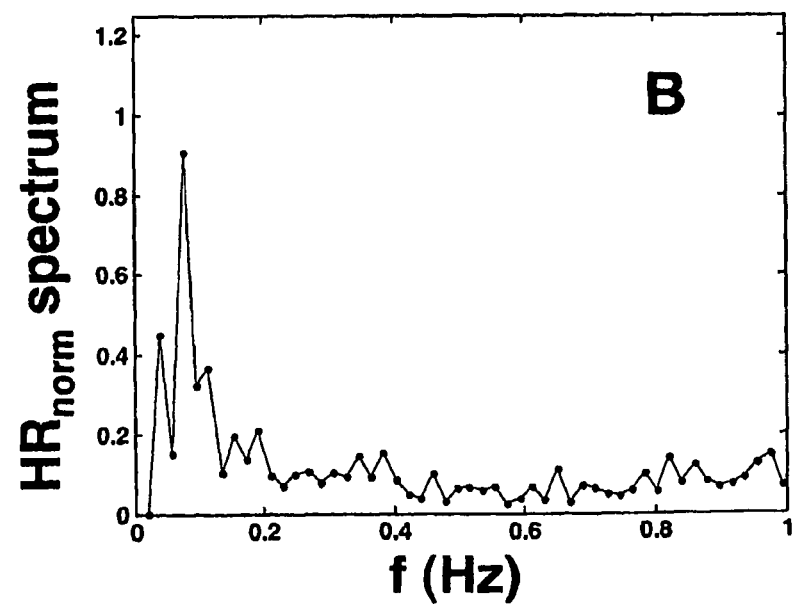

With an accurate fiducial point, the RR interval was measured in order to create time-domain variables. For the frequency domain metrics of the heart rate variability, sufficient frequency resolution was required while maintaining a time segment which was clinically relevant and in near real time. A 128 point fast Fourier transformation was chosen as the standard. Sixty-four (64) estimated points were provided over the positive frequency range and a data time segment less than 2 minutes long for the ranges of heart rates commonly found in children. Since the heart rate data was normalized, the mean is zero, and the sum of the power in the frequency bands is directly proportional to the variance. Therefore, ratios of power between bands (i.e., low/high frequency) are equal to variance ratios. The units of power are beats per minute $(bpm)^2/bpm^2$ (unit less) as opposed to $ms^2$, because of the use of the normalized heart rate data and not the heart beat period time series. The value for power reported within each frequency band varies but the ratios of interest were not affected. FIGS. 11A and 11B are graphs illustrating heart rate spectral curves for a surviving child and a child who died, respectively.

Figure 12:
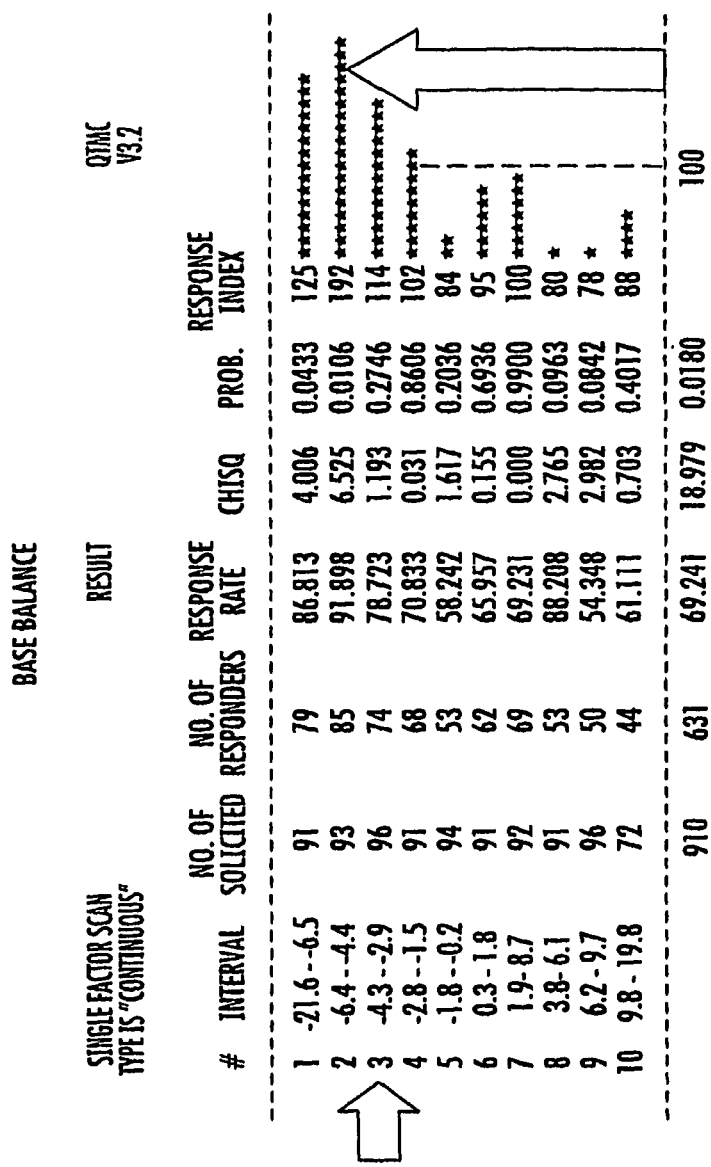
FIG. 12 is a chart profiling derogatory segments within variable (base excess) with a single factor scan.

Physiological based measures of organ function were defined by a battery of laboratory tests collected during the patients' PICU stay and a series of clinical signs and parameters (i.e., infusion of epinephrine) recorded by bedside PICU nurses. These tests were collected based upon clinical need which varied by patient and varied over time within each patient. A series of derogatory biomarkers were created to address the inclusion of this information with a reasonable patient-to-variable ratio and to manage an intercorrelation between tests. Only tests having identifiable segments with a high index for predicting mortality were included. This objective was achieved using a single factor scan procedure. FIG. 12 is a chart profiling derogatory segments within variable (base excess) with a single factor scan. The chart demonstrates that for patients with a base excess value of −4.4 to −6.4, there is an increase in mortality by 32% (response index=132). FIG. 13 is a chart profiling extreme derogatory ranges within a battery of laboratory tests. FIG. 14 is a chart illustrating an example of intermittent physiologic parameters and clinical signs. Further, FIG. 15 includes charts profiling examples of intermittent physiologic parameters and clinical signs evaluated through QTMS with selected best results.

Figure 16A:
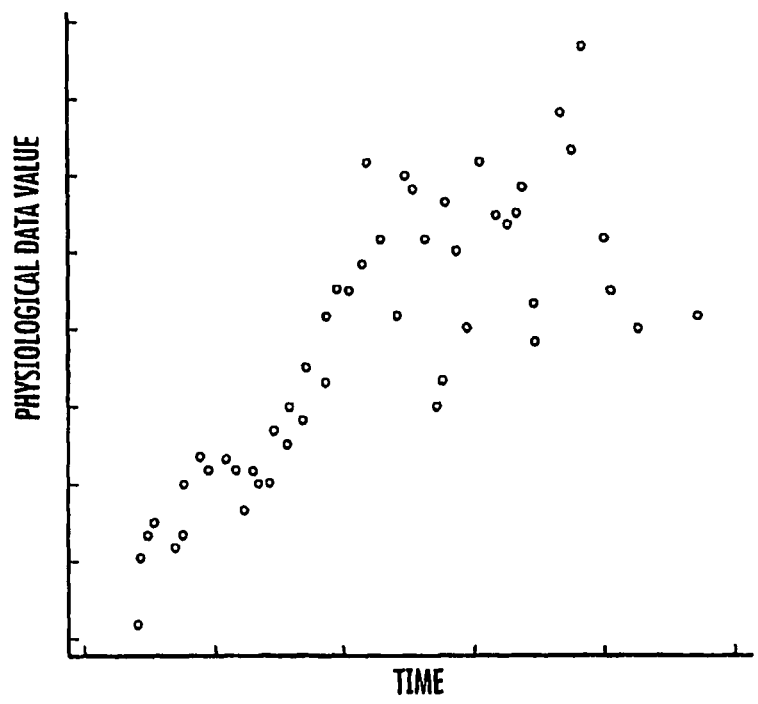
FIGS. 16A and 16B are graphs of intermittent original data and interpolated data in 2 minute increments, respectively.
Figure 16B:
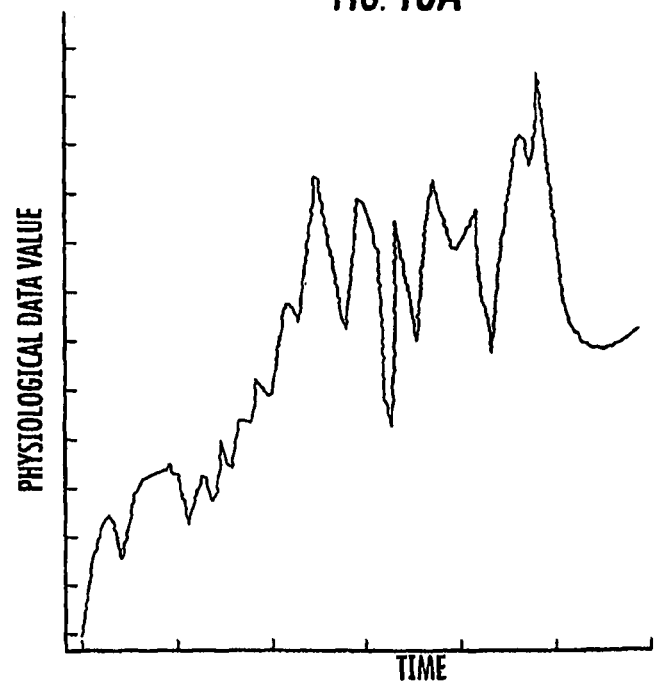

This experiment was an accumulation of multiple variables collected continuously, intermittently, or only once during a PICU stay. Thus, units of time for each class of variables were different. To link the 4 classes of variables, a common time frame of two minutes was utilized. The time series was combined with different frequencies using various interpolative methods. FIGS. 16A and 16B are graphs illustrating exemplary intermittent original data and interpolated data in 2 minute increments, respectively.

The first four hours of data from the 28 matched patients were partitioned out for analyses and outcome (i.e., dying patients versus surviving patients) recorded. This resulted in an analytic data set of 3360 records (1680 survive packets and 1680 died packets). Each patient thus produced 120 records for the first four hours at two minute intervals. A common time hierarchy file was analyzed using SAS® Enterprise Miner™ 5.1, which implemented 8 different modeling techniques using 80% of the PICU admission data packets. The different modeling techniques included a linear regression model, an autoneural network model, a logistic regression model, a DMneural model, a decision tree model, a neural network model, a minimum Bayes-risk (MBR) model, and a rule induction model. A random 20% hold out sample of packets were used to test a PICU admission model. In this experiment, the rule induction model most successfully classified patients who later survived or died based on the initial four hours of data after PICU admission.

Five clusters from the rule induction model that resulted in a risk of mortality score (between 0 and 100) were based on the segments of variables shown in Table 4 below.

TABLE 4

Individual Variable Segments Used in the Rule Induction Model

| Cluster 1 | Cluster 2 | Cluster 3 | Cluster 4 | Cluster 5 |
|---|---|---|---|---|
| O2Sat Art | pNN400 | Ionized Calcium | EPI | pNN600 |
| Sodium | pNN500 | PO2 <=57 | | |
| Base Balance | 2nd Derivative NN_Interval | O2Sat Art <=85.6 | | |
| PCO2 | Ionized Calcium | pNN400 | | |
| PO2 | O2Sat (Art) | | | |
| Bicarbonate | Sodium | | | |
| Base Balance <=−4.4 | | | | |
| Bicarbonate <=20.4 | | | | |
| Ionized Calcium | | | | |

Table 5 below shows the success of the model in relating the risk of mortality score (ranging between 0 and 100) to individual and cumulative mortality in training and validation PICU admission datasets.

TABLE 5

Risk of Mortality Score Associated with Mortality for Training and Validation Datasets

| | Training | | | Validation | |
|---|---|---|---|---|---|
| Risk of Mortality Score | Percent Mortality | Cumulative Mortality | Risk of Mortality Score | Percent Mortality | Cumulative Mortality |
| 5 | 100.0000 | 100.0000 | 5 | 100.0000 | 100.0000 |
| 10 | 100.0000 | 100.0000 | 10 | 100.0000 | 100.0000 |
| 15 | 100.0000 | 100.0000 | 15 | 100.0000 | 100.0000 |
| 20 | 100.0000 | 100.0000 | 20 | 100.0000 | 100.0000 |
| 25 | 100.0000 | 100.0000 | 25 | 100.0000 | 100.0000 |
| 30 | 100.0000 | 100.0000 | 30 | 100.0000 | 100.0000 |
| 35 | 100.0000 | 100.0000 | 35 | 100.0000 | 100.0000 |
| 40 | 98.5870 | 99.8230 | 40 | 96.4340 | 99.5540 |

TABLE 5-continued

Risk of Mortality Score Associated with Mortality for Training and Validation Datasets

| Training | | | Validation | | |
|---|---|---|---|---|---|
| Risk of Mortality Score | Percent Mortality | Cumulative Mortality | Risk of Mortality Score | Percent Mortality | Cumulative Mortality |
| 45 | 97.9620 | 99.6170 | 45 | 96.1540 | 99.1760 |
| 50 | 87.7480 | 98.4300 | 50 | 80.7100 | 97.3300 |
| 55 | 6.2110 | 90.0460 | 55 | 14.7060 | 89.8190 |
| 60 | 6.2110 | 83.0600 | 60 | 13.4820 | 83.4570 |
| 65 | 2.7900 | 76.8850 | 65 | 0.0000 | 77.0370 |
| 70 | 0.1180 | 71.4020 | 70 | 0.0000 | 71.5350 |
| 75 | 0.0000 | 66.6420 | 75 | 0.0000 | 62.5930 |
| 80 | 0.0000 | 62.4770 | 80 | 0.0000 | 62.5930 |
| 85 | 0.0000 | 58.8020 | 85 | 0.0000 | 58.9110 |
| 90 | 0.0000 | 52.6120 | 90 | 0.0000 | 55.6380 |
| 95 | 0.0000 | 52.6120 | 95 | 0.0000 | 52.7100 |
| 100 | 0.0000 | 49.9810 | 100 | 0.0000 | 50.0740 |

The table shows that for risk of mortality scores between 0 and 35, 100% of the patients die. For risk of mortality scores between 75 and 100, no patients die.

The predictive capabilities of the rule induction model are demonstrated in Tables 6 and 7 below, where the sensitivity of the model is 98.44% with a specificity of 98.88% in the training and validation datasets. In the training dataset, in 2687 two minute packets which were obtained in the first four hours after PICU admission, less than 3% were classified incorrectly (false positive rate=1.12% and false negative rate=1.56%). Similar results were found in the admission dataset, where sensitivity is 97.03% with a specificity of 98.21%.

TABLE 6

Training Dataset
Actual Patient Outcome

| | Survivor | Died | Total |
|---|---|---|---|
| Predicted to Survive | 1329 | 21 | 1350 |
| Predicted to Die | 15 | 1322 | 1337 |
| Total | 1344 | 1343 | 2687 |

TABLE 7

Validation Dataset
Actual Patient Outcome

| | Survivor | Died | Total |
|---|---|---|---|
| Predicted to Survive | 330 | 10 | 340 |
| Predicted to Die | 6 | 327 | 333 |
| Total | 336 | 337 | 673 |

Data obtained during the entire PICU length of stay (LOS) in the 28 patients has been analyzed. This data represents about 57,000 risk of mortality scores ranging from 0.29 to 12.73 days with a cumulative length of stay of 79.41 days for all patients. The predictive capabilities of the rule induction model are demonstrated in Table 8 below, where the model's sensitivity is 82.92% with a specificity of 71.32%.

TABLE 8

Classification for Total PICU LOS
Actual Patient Outcome

| | Survivor | Died | Total |
|---|---|---|---|
| Predicted to Survive | 17,248 | 5,636 | 22,884 |
| Predicted to Die | 6,936 | 27,354 | 34,290 |
| Total | 24,184 | 32,990 | 57,174 |

Six of the 14 survivors had 100% of the risk of mortality scores correct during the entire PICU LOS, while an additional 3 had greater than 80% correct risk of mortality predictions for this entire time period. Four of the 14 patient deaths had 100% of the risk of mortality scores correct during the entire PICU LOS, while an additional 6 had greater than 80% correct risk of mortality predictions for this entire time period. The incorrect predictions were either an error or a change in the physiological state of the patient such that during the specific two minute period, ultimate survivors appeared to be dying or ultimate deaths appeared to be improving.

Further, the data obtained during the final 4 hours in the PICU was analyzed in the 28 matched patients. The predictive capabilities of the rule induction model are demonstrated in Table 9 below.

TABLE 9

Classification for End of PICU Stay
Actual Patient Outcome

| | Survivor | Died | Total |
|---|---|---|---|
| Predicted to Survive | 1174 | 222 | 1396 |
| Predicted to Die | 506 | 1458 | 1964 |
| Total | 1680 | 1680 | 3360 |

Three of the 14 survivors had 100% of the risk of mortality scores correct during the final 4 hours, while an additional 5 had greater than 80% correct risk of mortality predictions for this time period. Seven of the 14 patient deaths had 100% of the risk of mortality scores correct during the final 4 hours, while an additional 4 had greater than 80% correct risk of mortality predictions from this time period.

An additional 16 survivors were analyzed during their entire PICU LOS. This data represents about 25,000 risk of mortality scores with LOS ranging from 0.23 to 6.36 days with 35.4 total patient days. The predictive capabilities of the rule induction model are demonstrated in Table 10 below.

TABLE 10

Classification for 16 Survivors During PICU LOS
Actual Patient Outcome

| | Survivor | Died | Total |
|---|---|---|---|
| Predicted to Survive | 20,080 | 0 | 20,080 |
| Predicted to Die | 5,411 | 0 | 5,411 |
| Total | 25,491 | 0 | 25,491 |

Two of the 16 survivors had 100% of the risk of mortality scores correct during the entire PICU LOS, while an additional 9 had greater than 80% correct risk of mortality predictions for this entire time period.

Figure 17:
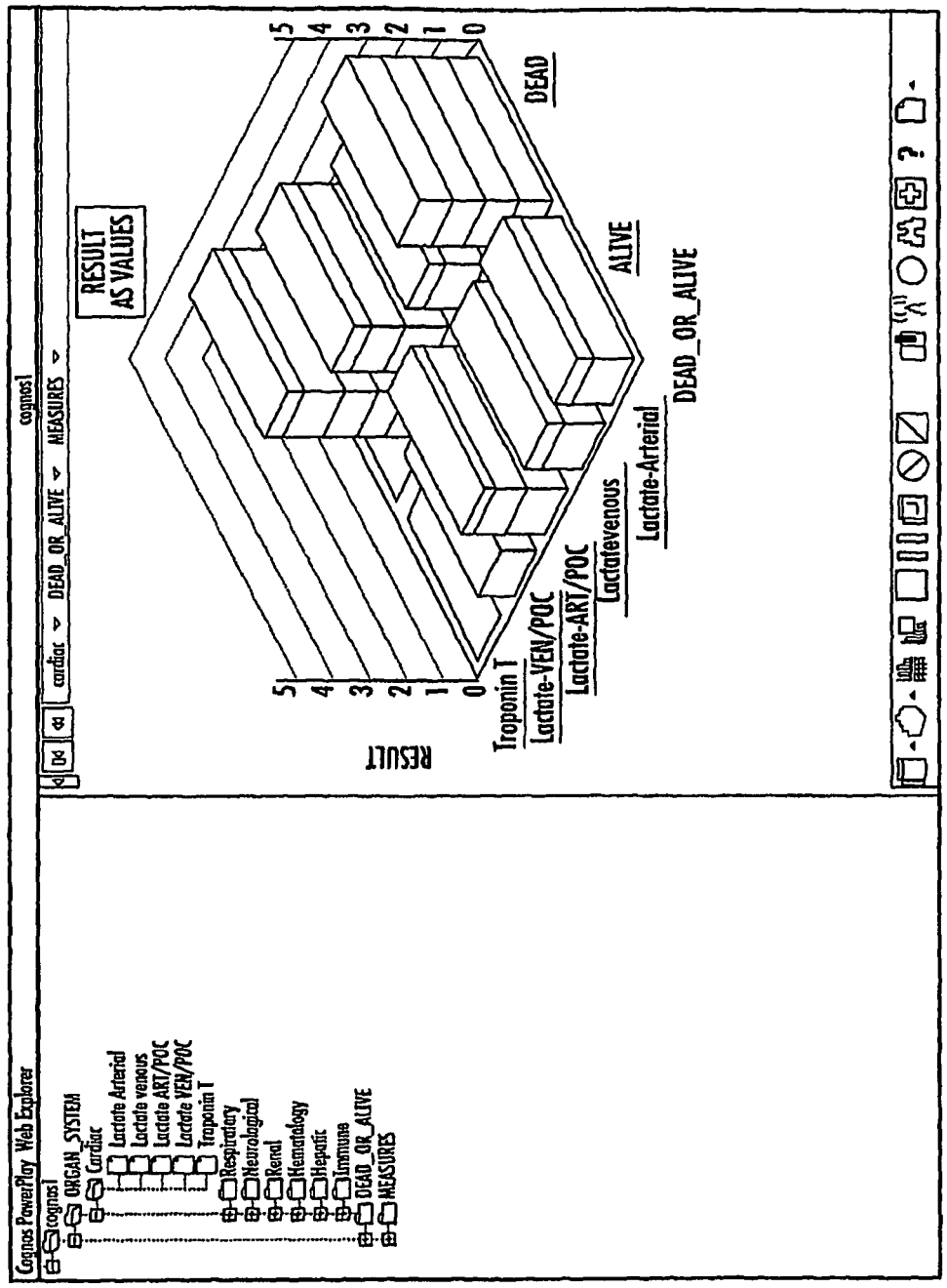
FIG. 17 is a screen display of an example of several cardiac variables for living and dead patients.

Software available from Cognos Incorporated, of Ottawa, Canada, was used for displayed the overall risk of mortality score and a color code of the score in 3 levels of risk of mortality. The color code includes red representing high risk, yellow representing medium risk, and green representing low risk. The individual variable were organized into 7 categories based on organ system with a drill down feature such that the individual variables contributing to the level of risk may be viewed in real time with updates every 2 minutes. FIG. 17 is a screen display illustrating an example of several cardiac variables (x-axis) for alive and dead patients (y-axis).

Selecting Physiological Variables

Evaluation of a patient may be improved by diversifying and expanding the physiological variables used in predicting a risk of mortality. According to an aspect of the subject matter disclosed herein, physiological variables with respect to risk of mortality may be selected for use in evaluating a risk of mortality of a patient in a PICU. A weight may be assigned to the physiological variable for use with a statistical model for determining a risk of mortality of the patient.

Figure 18:
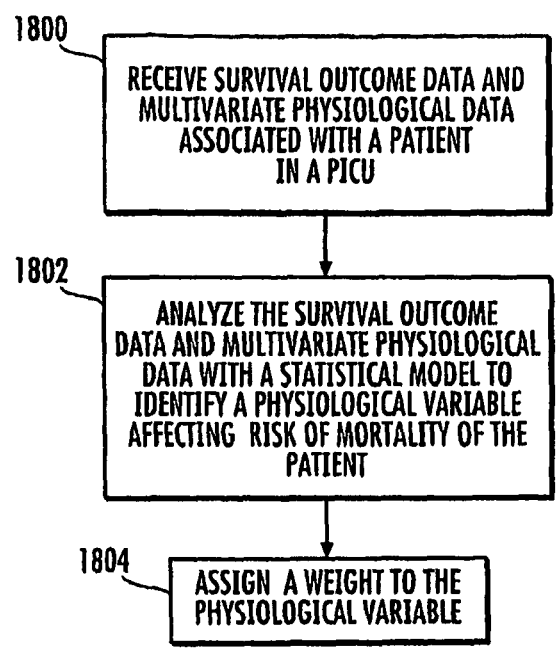
FIG. 18 is a flow chart of an exemplary process for selecting a physiological variable for use in evaluating risk of mortality of a patient in a PICU according to an embodiment of the subject matter described herein.

FIG. 18 is a flow chart illustrating an exemplary process for selecting a physiological variable for use in evaluating risk of mortality of a patient in a PICU according to an embodiment of the subject matter described herein. This exemplary process is described with reference to system 100 shown in FIG. 1. Referring to FIGS. 1 and 18, survival outcome data and multivariate physiological data associated with a patient in a PICU are received (block 1800). Survival outcome data may include data indicating whether one or more PICU patients survived or died while in the PICU. Multivariate physiological data may include the one or more patient's PICU heart rate data, blood pressure data, temperature, and/or any of the other types of physiological data disclosed herein. Data collector 114 may be configured to receive the survival outcome data and multivariate physiological data.

At block 1802, the survival outcome data and the multivariate physiological data are analyzed with a statistical model to identify a physiological variable affecting risk of mortality of the patient. For example, a rule induction model or any other suitable statistical model may be applied to the survival outcome data and the multivariate physiological data for identifying a physiological variable affecting the risk of mortality. One or more of the multivariate physiological data and/or trends of the physiological data may be determined to affect the risk of mortality. Mortality risk function 118 may be configured to analyze the data with the statistical model to identify a physiological variable affecting risk of mortality of the patient.

At block 1804, a weight may be assigned to the physiological variable for use with the statistical model for determining a risk of mortality of the patient. For example, heart rate variation in a particular range may be highly predictive of the risk of mortality of the patient. In this case, heart rate variation in the range may be assigned a large weight in the statistical model. Additional variables may be determined to affect the risk of mortality. Weights may be assigned to these variables based on their affect on the risk of mortality. Other variables may be assigned a weight of 0 if they do not affect the risk of mortality. Mortality risk function 118 may be configured to assign the physiological variable for use with the statistical model for determining a risk of mortality of the patient.

The SAS® Enterprise Miner™ 5.1 software may be used to calculate several multivariate models. A rule induction method may provide good replicated ROC using a 20% hold out sample. The rule induction method uses a neural clustering, which creates clusters based upon an orthogonal set of variables used to define each of them.

Figure 19:
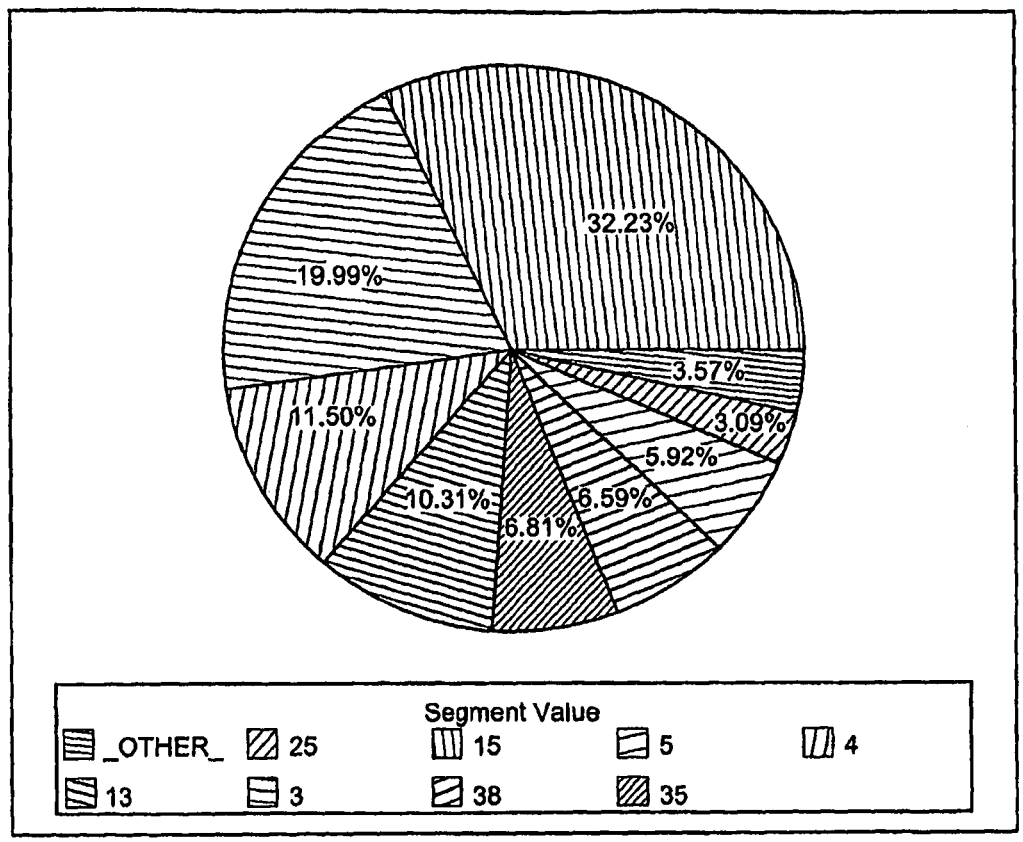
FIG. 19 is a pie chart of cluster sizes determined using a rule induction method.

An example of 8 cluster sizes are presented in the chart illustrated in FIG. 19. Each segment value is uniquely defined. The percentages shown in the chart correspond to the sizes of the segment values. Approximately 96% of all data may be categorized into the 8 clusters.

Figure 20:
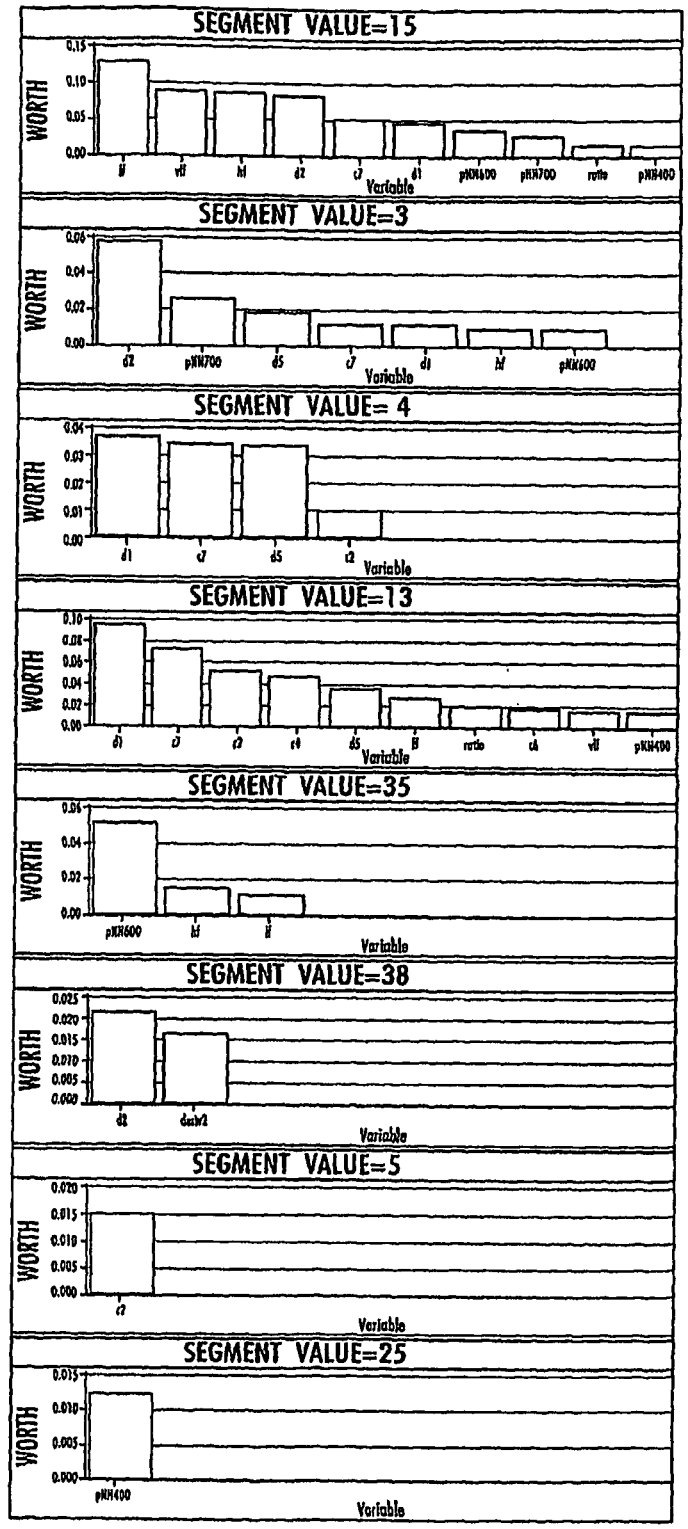
FIG. 20 includes bar graphs of a profile report for several clusters.
Figure 21A:
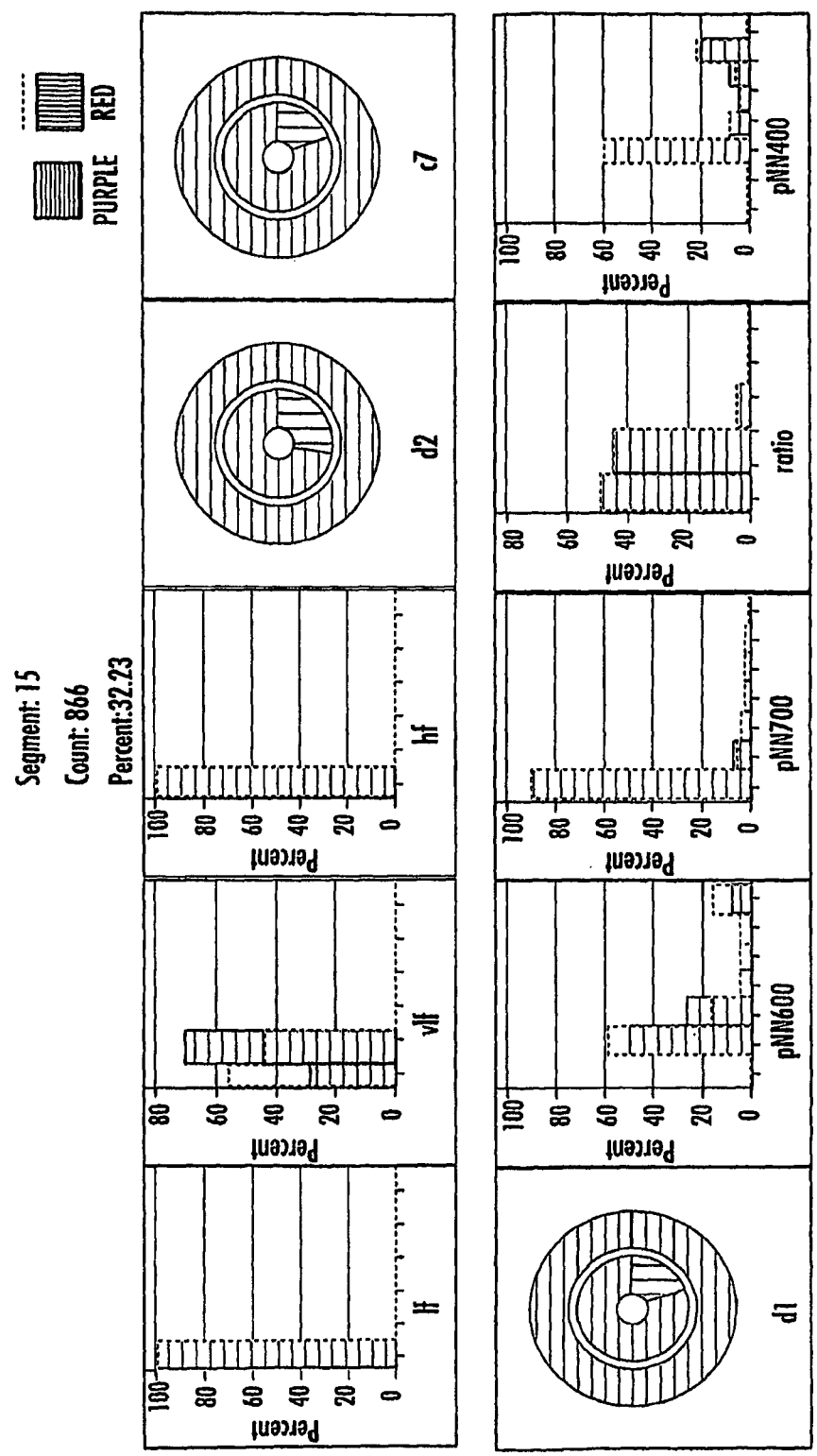
FIGS. 21A-21H includes graphs and charts detailing the ability of each cluster to differentiate between living and dead.
Figure 21B:
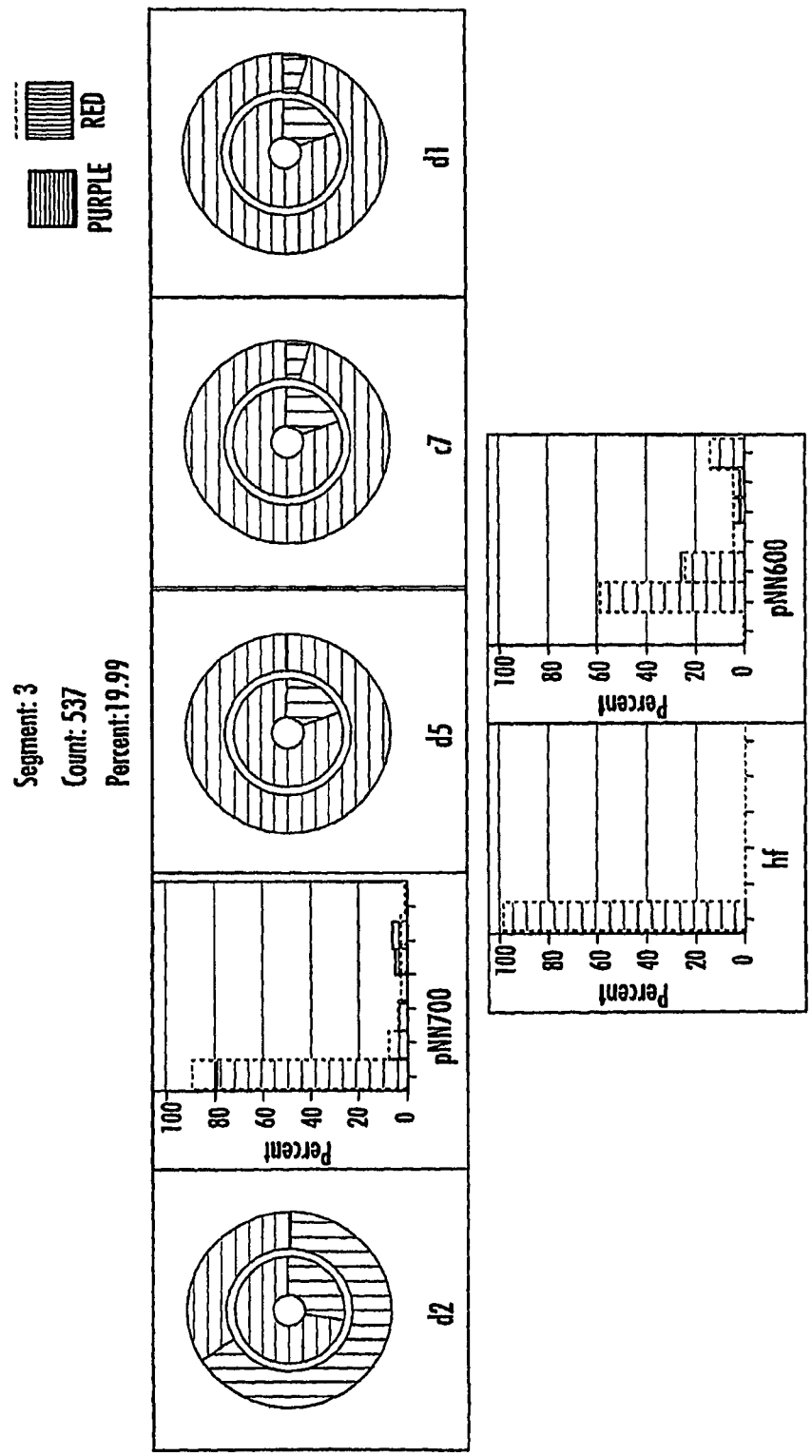
Figure 21C:
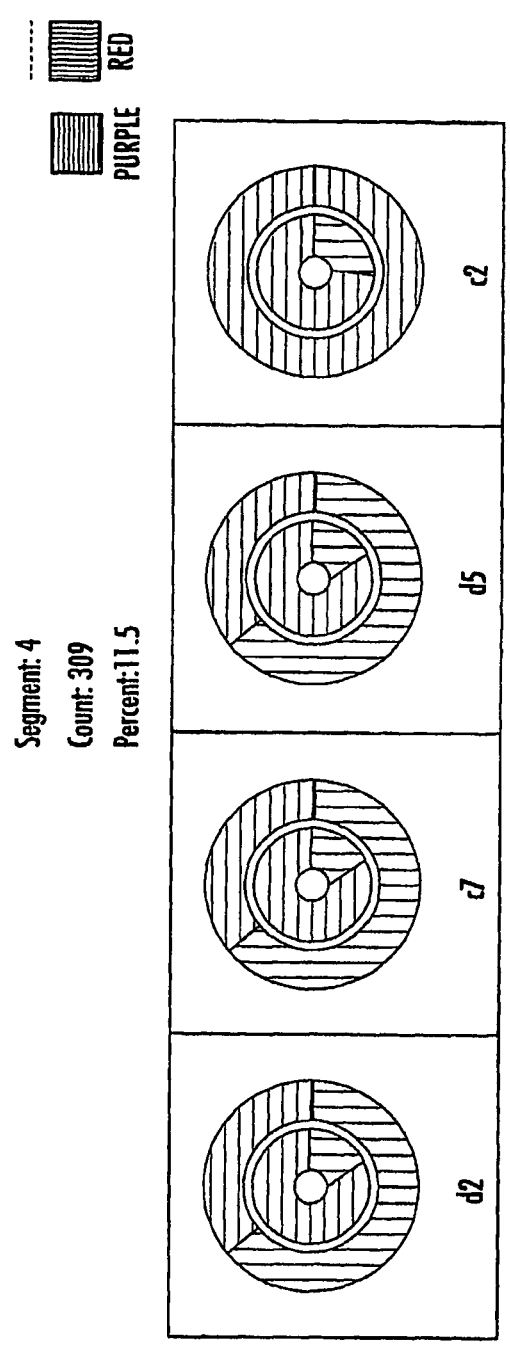
Figure 21D:
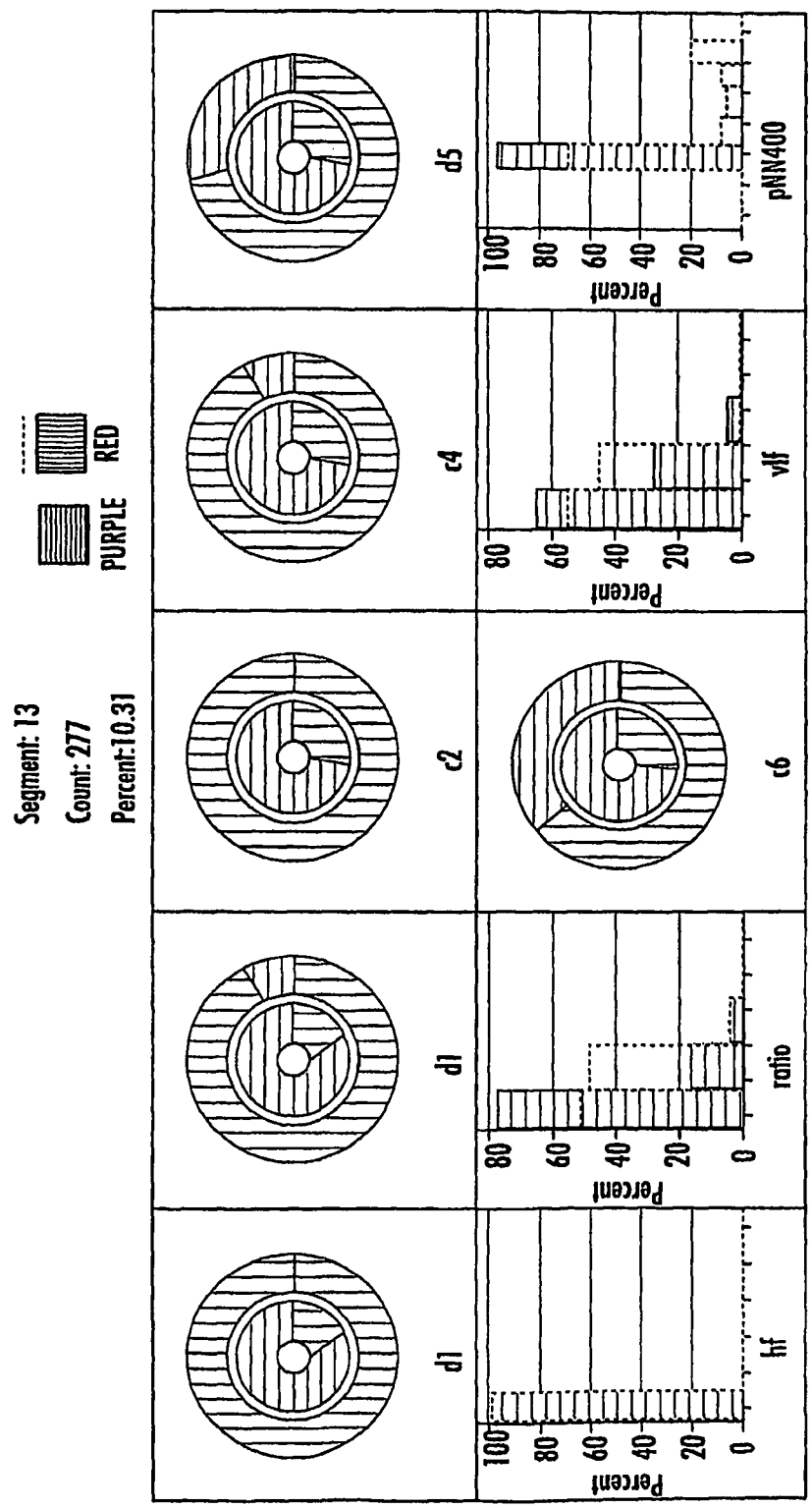
Figure 21E:
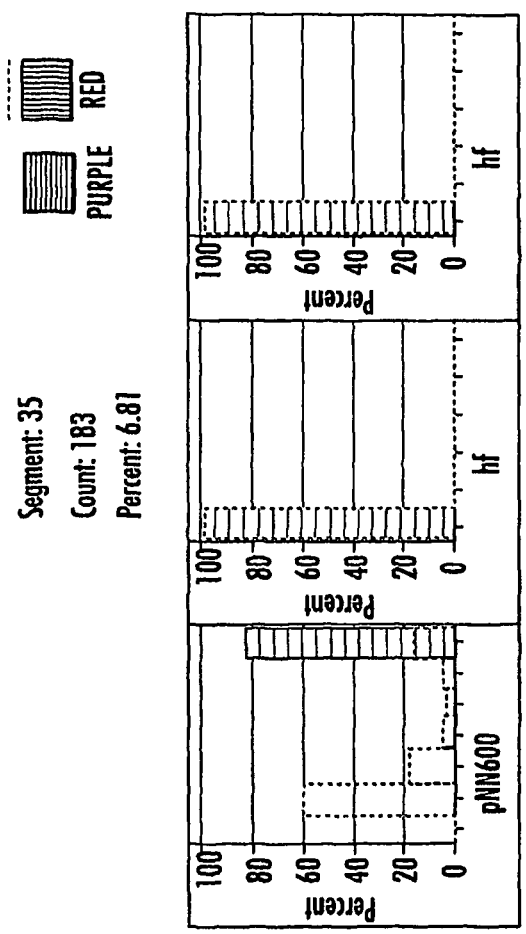
Figure 21F:
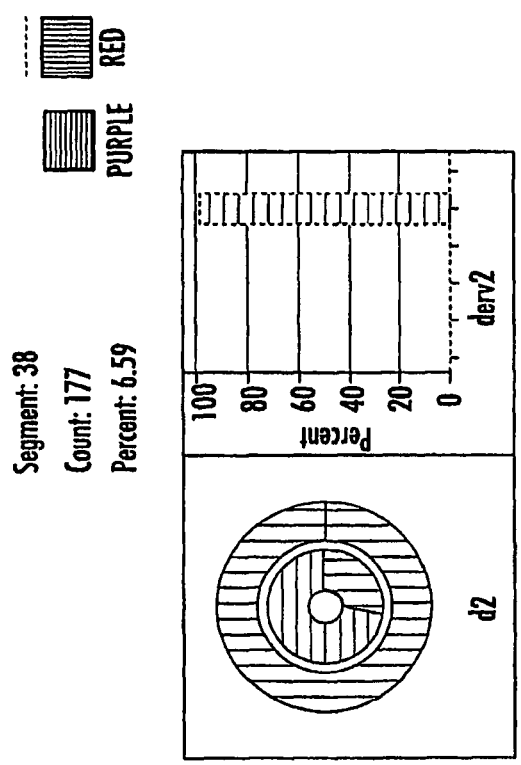
Figure 21G:
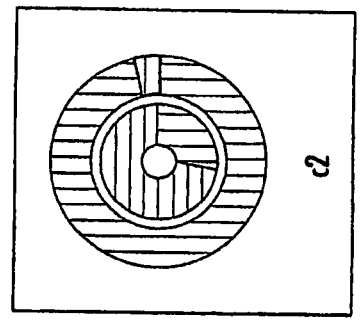
Figure 21H:
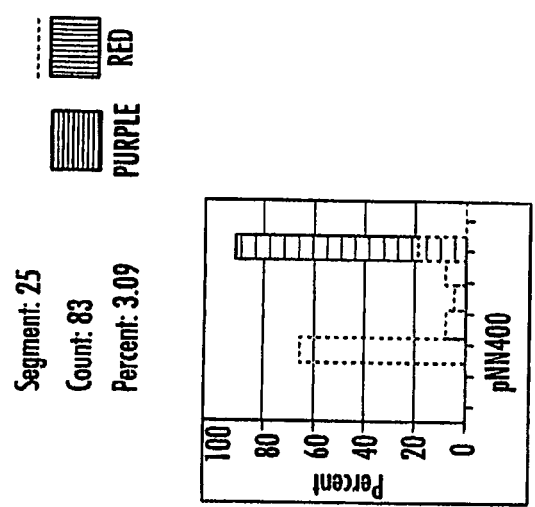

FIG. 20 includes bar graphs of a profile report for each cluster (in descending order of size). The data of FIG. 20 is associated with the data shown in FIG. 19. The profile report details the different set of variables used to define itself as a cluster.

FIGS. 21A-21H are graphs and charts detailing the ability of each cluster to differentiate between living and dead. The data of FIGS. 21A-21H is associated with the data shown in FIGS. 19 and 20. Referring to FIGS. 21A-21H, each graphic details the distributional characteristics between each cluster and the total sample. The inner circle in the pie charts represent the total sample, and the portions surrounding the inner circle represents the cluster characteristics for the pie charts. The outlined portion of the bar charts (represented by "red") represents the total sample. Segment "Other," which does not have a graphic shown in FIGS. 21A-21H, has a count 96 and a percentage of 3.57.

Figure 22:
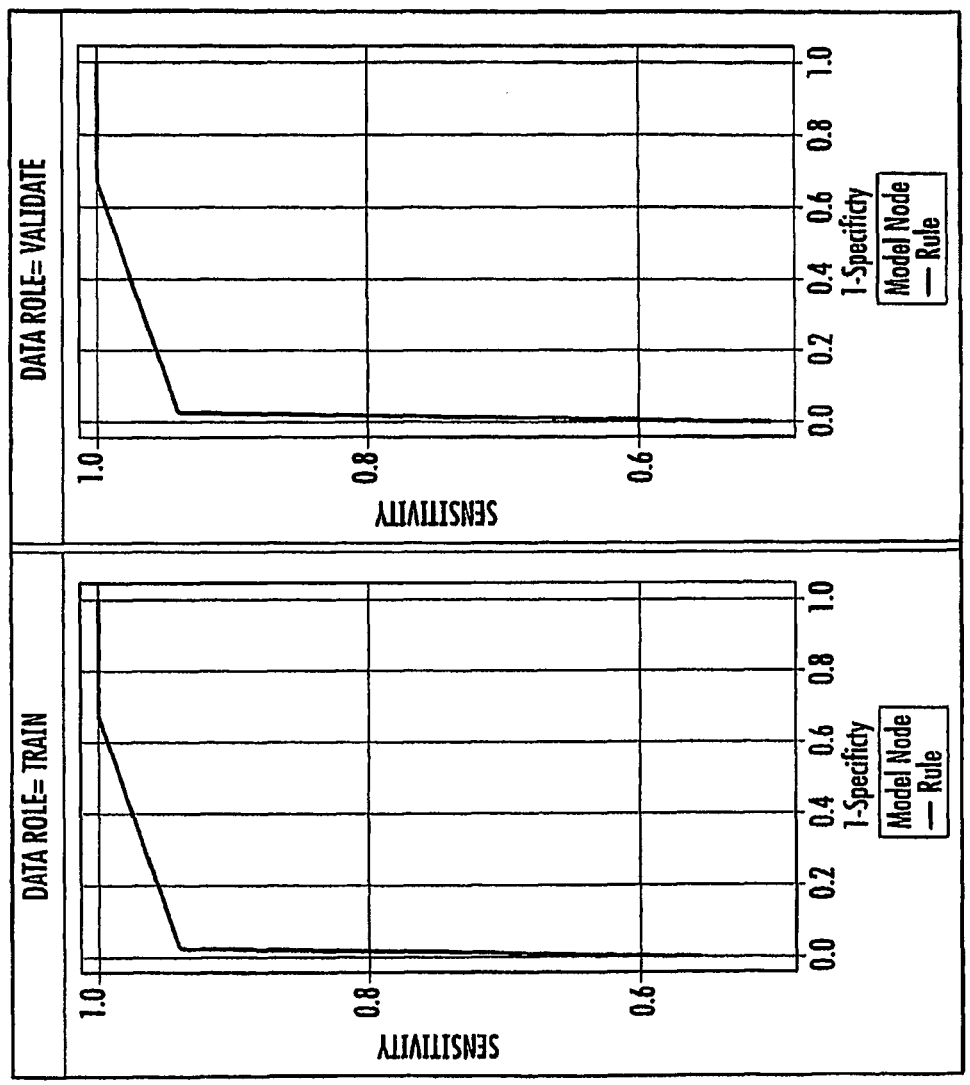
FIG. 22 includes graphs of receiver operator curves for the rule induction model.

FIG. 22 includes graphs of receiver operator curves for the rule induction model. Software code of a report summary detailing each cluster is provided below.

```
1
2
3
4
5
6
7
8
9
10   Variable Summary
11
12   ROLE             LEVEL              COUNT
13
14   ASSESS           NOMINAL            1
15   CLASSIFICATION   NOMINAL            2
16   INPUT            BINARY             10
17   INPUT            INTERVAL           9
18   PREDICT          INTERVAL           4
19   REJECTED         INTERVAL           1
20   SEGMENT          INTERVAL           1
21   TARGET           BINARY             1
22   TEXT             NOMINAL            1
23
24   Frequencies      NOMINAL            1
25
26                                              Percent of
27   Segment          Segment    Frequency       Total
28   Variable         Value        Count       Frequency
29
30   NODE                15         866         32.2293
31   NODE                 3         537         19.9851
32   NODE                 4         309         11.4998
33   NODE                13         277         10.3089
34   NODE                35         183          6.8106
35   NODE                38         177          6.5873
36   NODE                 5         159          5.9174
37   NODE                25          83          3.0889
38   NODE                25          96          3.5728
39
40   Variable: NODE Segment: 15 Count: 866
41   Decision Tree Importance Profiles
```

-continued

| Variable | Worth | Rank |
|---|---|---|
| lf | 0.12647 | 1 |
| vlf | 0.08865 | 2 |
| hf | 0.08692 | 3 |
| d2 | 0.08223 | 4 |
| c7 | 0.04926 | 5 |
| d1 | 0.04657 | 6 |
| pNN600 | 0.03478 | 7 |
| pNN700 | 0.02705 | 8 |
| ratio | 0.01498 | 9 |
| pNN400 | 0.01374 | 10 |

Variable: NODE Segment: 3 Count: 537
Decision Tree Importance Profiles

| Variable | Worth | Rank |
|---|---|---|
| d2 | 0.058262 | 1 |
| pNN700 | 0.026174 | 2 |
| d5 | 0.019032 | 3 |
| c7 | 0.012895 | 4 |
| d1 | 0.012859 | 5 |
| hf | 0.011065 | 6 |
| pNN600 | 0.010174 | 7 |

Variable: NODE Segment: 4 Count: 309
Decision Tree Importance Profiles

| Variable | Worth | Rank |
|---|---|---|
| d1 | 0.037565 | 1 |
| c7 | 0.034932 | 2 |
| d5 | 0.034219 | 3 |
| c2 | 0.010501 | 4 |

Variable: NODE Segment: 13 Count: 277
Decision Tree Importance Profiles

| Variable | Worth | Rank |
|---|---|---|
| d1 | 0.094825 | 1 |
| c7 | 0.071454 | 2 |
| c2 | 0.052342 | 3 |
| c4 | 0.046255 | 4 |
| d5 | 0.035796 | 5 |
| lf | 0.028111 | 6 |
| ratio | 0.019307 | 7 |
| c6 | 0.018488 | 8 |
| vlf | 0.015437 | 9 |
| pNN400 | 0.015101 | 10 |

Variable: NODE Segment: 35 Count 183
Decision Tree Importance Profiles

| Variable | Worth | Rank |
|---|---|---|
| pNN600 | 0.051863 | 1 |
| hf | 0.014300 | 2 |
| lf | 0.010793 | 3 |

Variable: NODE Segment: 38 Count: 177
Decision Tree Importance Profiles

| Variable | Worth | Rank |
|---|---|---|
| d2 | 0.021924 | 1 |
| deriv2 | 0.017044 | 2 |

Variable: NODE Segment: 5 Count: 159
Decision Tree Importance Profiles

| Variable | Worth | Rank |
|---|---|---|
| c2 | 0.015177 | 1 |

Variable: NODE Segment: 25 Count: 83
Decision Tree Importance Profiles

-continued

| Variable | Worth | Rank |
|---|---|---|
| pNN400 | 0.012530 | 1 |

Systems, methods, and computer program products disclosed herein may employ advanced computerized signal processing, statistical analyses, and neural network techniques to provide a continuously updated risk of mortality score in critically ill children. The score may serve as an early warning to changes in patient condition. Further, the score may guide the care of critically ill children. As a result, the mortality may be decreased and risk assessment of patients at admission may be improved. Further, medical practitioners may make more timely decisions about the rapid initiation or withdrawal of costly and risky therapeutic interventions.

Hospital costs may be reduced by better matching expensive and limited medical practitioner resources and hospital facilities to the changing needs of critically ill children. For example, services provided by physicians and nurses may be efficiently allocated. Further, for example, hospital liability risk may be lowered.

Other non-commercial benefits of the subject matter disclosed herein are provided to academic medical centers and society. For example, many PICUs are areas where physicians and nurses in training develop their clinical skills and complete their academic requirements. Systems and methods disclosed herein may assist them in recognizing impending death and learn how the initiation and withdrawal of therapies can return these children to health.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A patient monitoring system for determining a risk of mortality of a patient located in an intensive care unit, the system comprising:
   a plurality of medical sensors connected to the patient each configured to measure a physiological parameter and transmit related physiological data of the patient, the plurality of medical sensors including:
      a blood pressure medical sensor configured to measure a blood pressure physiological parameter, and
      a heart rate medical sensor configured to measure a heart rate physiological parameter; and
   a patient monitor communicatively coupled to the plurality of medical sensors and a hospital system, the patient monitor including:
      a user interface configured to receive an identifier of the patient,
      a data collector configured to periodically receive the physiological data from the plurality of medical sensors including blood pressure physiological data and heart rate physiological data,
      a mortality risk engine operating a mortality statistical model that is configured to determine the risk of mortality of the patient by:
         aggregating the physiological data from the medical sensors into regular defined time intervals related to when the physiological data was generated, and determining an ongoing risk of mortality of the patient, for each defined time interval, by:
(i) determining composite variable data from a transformation, derivative, or combination of the physiological data from the medical sensors,
(ii) identifying model parameters of the mortality statistical model that correspond to the composite variable data and the physiological data,
(iii) for each identified model parameter, identifying at least one significant fatal interval that has a numerical range of values and a mortality weight that is predicative of a fatal outcome for the patient for data that falls within the numerical range,
(iv) for each identified model parameter, determining there exists at least one significant non-fatal interval that has a numerical range of values and a mortality weight that is predicative of a non-fatal outcome for the patient for data that falls within the numerical range,
(v) for each identified model parameter, determining if the composite variable data or the physiological data that corresponds to the identified model parameter falls within the at least one significant fatal interval or the at least one significant non-fatal interval,
(vi) for the identified model parameters where the corresponding data from (v) falls within one of the intervals, averaging the mortality weights of those intervals to determine the risk of mortality of the patient, and
(vii) for the identified model parameters where the corresponding data from (v) does not fall within one of the intervals, discarding the corresponding data from consideration for determining the risk of mortality of the patient, and
a display interface configured to display the ongoing risk of mortality in numerical or graphical form in conjunction with at least some of the physiological data from some of the plurality of medical sensors.

2. The patient monitoring system of claim 1, wherein the data collector is configured to use the identifier of the patient to receive the physiological data from the plurality of medical sensors.

3. The patient monitoring system of claim 1, wherein at least one of the user interface and the data collector is configured to receive at least one of (a) an age, (b) a sex, and (c) a diagnosis of the patient, and
wherein the mortality risk engine is configured to adjust at least one of the at least one significant fatal interval and the at least one significant non-fatal interval based on the at least one of (a), (b), and (c).

4. The patient monitoring system of claim 1, wherein the mortality risk engine is configured to determine the composite variable data of the heart rate physiological data by performing a spectral analysis of heart rate variability by:
determining low frequency spectral content of the heart rate variability;
determining high frequency spectral content of the heart rate variability; and
determining a ratio of the low frequency spectral content to the high frequency spectral content.

5. The patient monitoring system of claim 1, wherein the mortality risk engine is configured to determine the composite variable data by calculating at least one nonlinear trend within the physiological data.

6. The patient monitoring system of claim 1, wherein the mortality risk engine is configured to determine the composite variable data of the heart rate physiological data and the blood pressure physiological data by performing a power spectral analysis of arterial blood pressure by:
determining a first power trend in a first low frequency band within the heart rate physiological data; and
determining a second power trend in a second low frequency band within the blood pressure physiological data.

7. A patient monitoring method for determining a risk of mortality of a patient, the method comprising:
receiving, in a data collector, physiological data from medical sensors connected to the patient including:
blood pressure physiological data from a blood pressure medical sensor configured to measure a blood pressure physiological parameter, and
heart rate physiological data and a blood pressure medical sensor configured to measure a blood pressure physiological parameter;
operating, in a mortality risk processor, a mortality statistical model that is configured to determine the risk of mortality of the patient by:
aggregating the physiological data from the medical sensors into regular defined time intervals related to when the physiological data was generated, and
determining an ongoing risk of mortality of the patient, for each defined time interval, by:
(i) determining composite variable data from a transformation, derivative, or combination of the aggregated physiological data from the medical sensors,
(ii) identifying model parameters of the mortality statistical model that correspond to the composite variable data and the aggregated physiological data,
(iii) for each identified model parameter, identifying at least one significant fatal interval that has a numerical range of values and a mortality weight that is predicative of a fatal outcome for the patient for the aggregated physiological data that falls within the numerical range,
(iv) for each identified model parameter, determining there exists at least one significant non-fatal interval that has a numerical range of values and a mortality weight that is predicative of a non-fatal outcome for the patient for the aggregated physiological data that falls within the numerical range,
(v) for each identified model parameter, determining if the composite variable data or the aggregated physiological data that corresponds to the identified model parameter falls within the at least one significant fatal interval or the at least one significant non-fatal interval,
(vi) for the identified model parameters where the corresponding data from (v) falls within one of the intervals, averaging the mortality weights of those intervals to determine the risk of mortality of the patient, and
(vii) for the identified model parameters where the corresponding data from (v) does not fall within one of the intervals, discarding the corresponding data from consideration for determining the risk of mortality of the patient; and
displaying, via an interface communicatively coupled to the mortality risk processor, the ongoing risk of mortality in numerical or graphical form in conjunction with at least some of the physiological data from some of the plurality of medical sensors.

8. The patient monitoring method of claim 7, further comprising receiving, in the data collector, physiological data as at least one of demographic data and diagnosis from at least one of a patient chart and a laboratory test related to the patient.

9. The patient monitoring method of claim 8, wherein the demographic data includes at least one a patient age, a patient sex, and a patient weight, and wherein the diagnosis data includes at least one of a chromosomal abnormality, an oncologic disease, an acute diabetic complication, a nonoperative cardiovascular disease, a previous admission for current hospitalization, a pre-ICU cardiopulmonary resuscitation, a transfer from an inpatient unit, a post operative status, a presence of cyanotic heart disease, and a presence of permanent or temporary cardiac pacing.

10. The patient monitoring method of claim 7, wherein a first defined time interval occurs at admittance of the patient to a hospital and subsequent defined time intervals occur after admittance.

11. The patient monitoring method of claim 7, wherein a first set of the defined time intervals occurs before a treatment on the patient and a second set of the defined time intervals occurs after the treatment.

12. The patient monitoring method of claim 11, further comprising determining at least one of (a) an effectiveness of the treatment, and (b) a patient's response to the treatment, by comparing the ongoing risk of mortality from the first set of defined time intervals to the ongoing risk of mortality from the second set of defined time intervals.

13. The patient monitoring method of claim 7, further comprising using the ongoing risk of mortality to treat the patient.

14. The patient monitoring method of claim 7, wherein the mortality risk engine is configured to determine the composite variable data from the physiological data using a bispectral method to determine at least one nonlinear trend within the physiological data.

15. A patient monitoring apparatus for determining a risk of mortality of a patient, the apparatus comprising:
  a data collector communicatively coupled to medical sensors connected to the patient, each of the sensors configured to measure a physiological parameter and transmit related physiological data of the patient, the data collector configured to periodically receive the physiological data from the medical sensors;
  a mortality risk engine operating a mortality statistical model that is configured to determine the risk of mortality of the patient by:
    aggregating the physiological data from the medical sensors into regular defined time intervals related to when the physiological data was generated, and
    determining an ongoing risk of mortality of the patient, for each defined time interval, by:
      (i) determining composite variable data from a transformation, derivative, or combination of the aggregated physiological data from the medical sensors,
      (ii) identifying model parameters of the mortality statistical model that correspond to the composite variable data and the aggregated physiological data,
      (iii) for each identified model parameter, identifying at least one significant fatal interval that has a numerical range of values and a mortality weight that is predicative of a fatal outcome for the patient for the aggregated physiological data that falls within the numerical range,
      (iv) for each identified model parameter, determining there exists at least one significant non-fatal interval that has a numerical range of values and a mortality weight that is predicative of a non-fatal outcome for the patient for the aggregated physiological data that falls within the numerical range,
      (v) for each identified model parameter, determining if the composite variable data or the aggregated physiological data that corresponds to the identified model parameter falls within the at least one significant fatal interval or the at least one significant non-fatal interval,
      (vi) for the identified model parameters where the corresponding data from (v) falls within one of the intervals, averaging the mortality weights of those intervals to determine the risk of mortality of the patient, and
      (vii) for the identified model parameters where the corresponding data from (v) does not fall within one of the intervals, discarding the corresponding data from consideration for determining the risk of mortality of the patient; and
  a display interface configured to display the ongoing risk of mortality in numerical or graphical form in conjunction with at least some of the physiological data from some of the medical sensors.

16. The patient monitoring apparatus of claim 15, wherein the apparatus is included within a pediatric intensive care unit or an intensive care unit.

17. The patient monitoring apparatus of claim 15, wherein the mortality risk engine is configured to:
  compare the ongoing risk of mortality to a predetermined level, and
  responsive to the ongoing risk of mortality exceeding the predetermined level, generate an alarm.

18. The patient monitoring apparatus of claim 17, wherein the mortality risk engine is configured to generate the alarm by at least one of:
  causing the display interface to display an icon indicative of the alarm, and
  communicating the alarm to a computer.

19. The patient monitoring apparatus of claim 15, wherein the data collector is configured to receive at least one of electrocardiogram (ECG) physiological data, temperature physiological data, heart rate physiological data, blood pressure physiological data, central venous pressure physiological data, pulsed oximetry physiological data, carbon dioxide concentration physiological data, respiratory rate physiological data, and an oxygen saturation physiological data.

20. The patient monitoring apparatus of claim 15, wherein the ongoing risk of mortality is used to determine a clinical status of the patient.

* * * * *